(12) United States Patent
Liu et al.

(10) Patent No.: US 11,104,967 B2
(45) Date of Patent: Aug. 31, 2021

(54) EVOLUTION OF SITE-SPECIFIC RECOMBINASES

(71) Applicant: President and Fellows of Harvard College, Cambridge, MA (US)

(72) Inventors: David R. Liu, Lexington, MA (US); David B. Thompson, Brookline, MA (US); Jeffrey L. Bessen, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 105 days.

(21) Appl. No.: 16/521,371

(22) Filed: Jul. 24, 2019

(65) Prior Publication Data

US 2020/0071722 A1  Mar. 5, 2020

Related U.S. Application Data

(62) Division of application No. 15/216,844, filed on Jul. 22, 2016, now Pat. No. 10,392,674.
(Continued)

(51) Int. Cl.
*C40B 30/04* (2006.01)
*C12Q 1/6876* (2018.01)
(Continued)

(52) U.S. Cl.
CPC .......... *C12Y 207/07* (2013.01); *C12N 9/1241* (2013.01); *C12N 15/1037* (2013.01);
(Continued)

(58) Field of Classification Search
None
See application file for complete search history.

(56) References Cited

U.S. PATENT DOCUMENTS 5,057,432 A   10/1991  Wangersky et al.
5,223,409 A    6/1993  Ladner et al.
(Continued)

FOREIGN PATENT DOCUMENTS

EP   3115457 A1   1/2017
JP   H0937764 A   2/1997
(Continued)

OTHER PUBLICATIONS

Extended European Search Report, dated Mar. 30, 2012, in connection with Application No. EP 09812363.
(Continued)

*Primary Examiner* — Christian C Boesen
(74) *Attorney, Agent, or Firm* — Wolf, Greenfield & Sacks, P.C.

(57) ABSTRACT

Some aspects of the present disclosure provide methods for evolving recombinases to recognize target sequences that differ from the canonical recognition sequences. Some aspects of this disclosure provide evolved recombinases, e.g., recombinases that bind and recombine naturally-occurring target sequences, such as, e.g., target sequences within the human Rosa26 locus. Methods for using such recombinases for genetically engineering nucleic acid molecules in vitro and in vivo are also provided. Some aspects of this disclosure also provide libraries and screening methods for assessing the target site preferences of recombinases, as well as methods for selecting recombinases that bind and recombine a non-canonical target sequence with high specificity.

10 Claims, 20 Drawing Sheets

Specification includes a Sequence Listing.

Related U.S. Application Data

(60) Provisional application No. 62/195,739, filed on Jul. 22, 2015.

(51) Int. Cl.

| | | |
|---|---|---|
| *C12N 9/12* | (2006.01) | |
| *C12N 15/10* | (2006.01) | |
| *C12N 15/86* | (2006.01) | |
| *C40B 40/10* | (2006.01) | |
| *C12N 15/90* | (2006.01) | |

(52) U.S. Cl.
CPC ..... *C12N 15/1058* (2013.01); *C12N 15/1093* (2013.01); *C12N 15/86* (2013.01); *C12Q 1/6876* (2013.01); *C40B 30/04* (2013.01); *C12N 15/907* (2013.01); *C12N 2795/00021* (2013.01); *C12N 2795/00043* (2013.01); *C12N 2795/14121* (2013.01); *C12N 2795/14143* (2013.01); *C40B 40/10* (2013.01)

(56) References Cited

U.S. PATENT DOCUMENTS

| | | |
|---|---|---|
| 5,658,727 A | 8/1997 | Barbas et al. |
| 5,712,089 A | 1/1998 | Borrebaeck et al. |
| 5,821,047 A | 10/1998 | Garrard et al. |
| 5,965,124 A | 10/1999 | Feinberg et al. |
| 6,156,509 A | 12/2000 | Schellenberger |
| 6,429,298 B1 | 8/2002 | Ellington et al. |
| 6,969,731 B1 | 11/2005 | Tang et al. |
| 9,023,594 B2 | 5/2015 | Liu et al. |
| 9,228,207 B2 | 1/2016 | Liu et al. |
| 9,267,127 B2 | 2/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,394,537 B2 | 7/2016 | Liu et al. |
| 9,526,784 B2 | 12/2016 | Liu et al. |
| 9,567,589 B2 | 2/2017 | Jin et al. |
| 9,737,604 B2 | 8/2017 | Jin et al. |
| 9,766,216 B2 | 9/2017 | Wada et al. |
| 9,771,574 B2 | 9/2017 | Liu et al. |
| 10,179,911 B2 | 1/2019 | Liu et al. |
| 10,227,581 B2 | 3/2019 | Liu et al. |
| 10,336,997 B2 | 7/2019 | Liu et al. |
| 10,392,674 B2 | 8/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |
| 10,920,208 B2 | 2/2021 | Liu et al. |
| 2002/0132327 A1 | 9/2002 | Hay et al. |
| 2003/0119764 A1 | 6/2003 | Loeb et al. |
| 2003/0167533 A1 | 9/2003 | Yadav et al. |
| 2003/0203480 A1 | 10/2003 | Kovesdi et al. |
| 2005/0019753 A1 | 1/2005 | Kukolj et al. |
| 2005/0100973 A1 | 5/2005 | Steward et al. |
| 2006/0160222 A1 | 7/2006 | Rozwadowski et al. |
| 2006/0166319 A1 | 7/2006 | Chan et al. |
| 2008/0220502 A1 | 9/2008 | Schellenberger et al. |
| 2009/0215110 A1 | 8/2009 | Gibson et al. |
| 2009/0227463 A1 | 9/2009 | Reif et al. |
| 2009/0300777 A1 | 12/2009 | Nakayama |
| 2010/0297180 A1 | 11/2010 | Shone |
| 2011/0177495 A1 | 7/2011 | Liu et al. |
| 2012/0128649 A1 | 5/2012 | Chaddock et al. |
| 2013/0059931 A1 | 3/2013 | Petersen-Mahrt et al. |
| 2013/0117869 A1 | 5/2013 | Duchateau et al. |
| 2013/0345064 A1 | 12/2013 | Liu et al. |
| 2013/0345065 A1 | 12/2013 | Liu et al. |
| 2014/0201858 A1 | 7/2014 | Ostertag et al. |
| 2015/0056177 A1 | 2/2015 | Liu et al. |
| 2015/0259721 A1 | 9/2015 | Van Brunt et al. |
| 2015/0275202 A1 | 10/2015 | Liu et al. |
| 2016/0002301 A1 | 1/2016 | Je et al. |
| 2016/0201040 A1 | 7/2016 | Liu et al. |
| 2016/0348096 A1 | 12/2016 | Liu et al. |
| 2017/0009224 A1 | 1/2017 | Liu et al. |
| 2017/0029844 A1 | 2/2017 | Ball et al. |
| 2017/0044520 A1 | 2/2017 | Liu et al. |
| 2017/0233708 A1 | 8/2017 | Liu et al. |
| 2018/0057545 A9 | 3/2018 | Liu et al. |
| 2018/0087046 A1 | 3/2018 | Liu et al. |
| 2018/0237758 A1 | 8/2018 | Liu et al. |
| 2019/0219575 A1 | 7/2019 | Gray et al. |
| 2019/0256842 A1 | 8/2019 | Liu et al. |
| 2019/0276816 A1 | 9/2019 | Liu et al. |
| 2019/0276873 A1 | 9/2019 | Dong et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |

FOREIGN PATENT DOCUMENTS

| | | |
|---|---|---|
| JP | 2011-081011 | 4/2011 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 94/18316 A2 | 8/1994 |
| WO | WO 96/04403 A1 | 2/1996 |
| WO | WO 98/32845 A1 | 7/1998 |
| WO | WO 00/71694 A1 | 11/2000 |
| WO | WO 01/05950 A2 | 1/2001 |
| WO | WO 01/61049 A1 | 8/2001 |
| WO | WO 2005/081632 A2 | 9/2005 |
| WO | WO 2007/066923 A1 | 6/2007 |
| WO | WO 2008/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/039518 A2 | 4/2011 |
| WO | WO 2011/147590 A2 | 12/2011 |
| WO | WO 2011/066747 A1 | 6/2012 |
| WO | WO 2012/088381 A2 | 6/2012 |
| WO | WO 2012/138927 A2 | 10/2012 |
| WO | WO 2013/047844 A1 | 4/2013 |
| WO | WO 2014/039585 A2 | 3/2014 |
| WO | WO 2014/157820 A1 | 10/2014 |
| WO | WO 2014/158593 A1 | 10/2014 |
| WO | WO 2015/134121 A2 | 9/2015 |
| WO | WO 2015/193897 A1 | 12/2015 |
| WO | WO 2016/077052 A9 | 5/2016 |
| WO | WO 2016/168631 A1 | 10/2016 |
| WO | WO 2017/015559 A2 | 1/2017 |
| WO | WO 2017/070632 A2 | 4/2017 |
| WO | WO 2018/009903 A2 | 1/2018 |
| WO | WO 2018/027078 A1 | 2/2018 |
| WO | WO 2018/039438 A1 | 3/2018 |
| WO | WO 2018/109447 A1 | 6/2018 |
| WO | WO 2018/136939 A1 | 7/2018 |
| WO | WO 2019/040935 A1 | 2/2019 |
| WO | WO 2019/067815 A2 | 4/2019 |

OTHER PUBLICATIONS

Extended European Search Report, dated May 26, 2017, in connection with Application No. EP 16 20 3684.

International Search Report and Written Opinion, dated Jun. 21, 2010, in connection with Application No. PCT/US2009/056194.

International Preliminary Report on Patentability, dated Mar. 17, 2011, in connection with Application No. PCT/US2009/056194.

Extended European Search Report, dated May 16, 2017, in connection with Application No. EP 17 16 0955.

Invitation to Pay Additional Fees, dated Aug. 30, 2012, in connection with Application No. PCT/US2011/066747.

International Search Report and Written Opinion, dated Oct. 30, 2012, in connection with Application No. PCT/US2011/066747.

(56) References Cited

OTHER PUBLICATIONS

International Preliminary Report on Patentability, dated Jul. 4, 2013, in connection with Application No. PCT/US2011/066747.
International Search Report and Written Opinion, dated Jan. 30, 2015, in connection with Application No. PCT/US2014/052231.
International Preliminary Report on Patentability, dated Mar. 3, 2016, in connection with Application No. PCT/US2014/052231.
International Search Report and Written Opinion, dated Sep. 25, 2015, in connection with Application No. PCT/US2015/012022.
International Preliminary Report on Patentability, dated Aug. 4, 2016, in connection with Application No. PCT/US2015/012022.
Invitation to Pay Additional Fees, dated Jan. 12, 2017, in connection with Application No. PCT/US/2016/043559.
International Search Report and Written Opinion, dated Mar. 10, 2017, in connection with Application No. PCT/US/2016/043559.
International Preliminary Report on Patentability, dated Feb. 1, 2018, in connection with Application No. PCT/US/2016/043559.
International Search Report and Written Opinion, dated Jun. 10, 2016, in connection with Application No. PCT/US2015/057012.
International Preliminary Report on Patentability, dated May 4, 2017, in connection with Application No. PCT/US2015/057012.
International Search Report and Written Opinion, dated Aug. 11, 2016, in connection with Application No. PCT/US2016/027795.
International Preliminary Report on Patentability, dated Oct. 26, 2017, in connection with Application No. PCT/US2016/027795.
Invitation to Pay Additional Fees, dated Oct. 12, 2016, in connection with Application No. PCT/US2016/044546.
International Search Report and Written Opinion, dated Dec. 28, 2016, in connection with Application No. PCT/US2016/044546.
International Preliminary Report on Patentability, dated Feb. 8, 2018, in connection with Application No. PCT/US/2016/044546.
International Search Report and Written Opinion, dated Nov. 30, 2016, in connection with Application No. PCT/US2016/043513.
International Preliminary Report on Patentability, dated Feb. 1, 2018, in connection with Application No. PCT/US2016/043513.
Invitation to Pay Additional Fees, dated Apr. 5, 2018, in connection with Application No. PCT/US2018/14867.
International Search Report and Written Opinion, dated May 23, 2018, in connection with Application No. PCT/US2018/14867.
International Preliminary Report on Patentability, dated Aug. 1, 2019, in connection with Application No. PCT/US2018/14867.
Invitation to Pay Additional Fees, dated Sep. 12, 2018, in connection with Application No. PCT/US2018/040692.
International Search Report and Written Opinion, dated Nov. 15, 2018, in connection with Application No. PCT/US2018/040692.
International Preliminary Report on Patentability, dated Jan. 16, 2020, in connection with Application No. PCT/US2018/040692.
Invitation to Pay Additional Fees, dated Jan. 4, 2019, in connection with Application No. PCT/US2018/051557.
International Search Report and Written Opinion, dated Feb. 25, 2019, in connection with Application No. PCT/US2018/051557.
International Preliminary Report on Patentability, dated Apr. 2, 2020, in connection with Application No. PCT/US2018/051557.
International Search Report and Written Opinion, dated Nov. 21, 2018, in connection with Application No. PCT/US2018/044242.
International Search Report and Written Opinion, dated Sep. 4, 2019, in connection with Application No. PCT/US2019/037216.
International Preliminary Report on Patentability, dated Dec. 24, 2020, in connection with Application No. PCT/US2019/037216.
Invitation to Pay Additional Fees, dated Nov. 19, 2018, in connection with Application No. PCT/US18/48134.
International Search Report and Written Opinion, dated Jan. 22, 2019, in connection with Application No. PCT/US18/48134.
International Preliminary Report on Patentability, dated Mar. 5, 2020, in connection with Application No. PCT/US18/48134.
Invitation to Pay Additional Fees, dated Oct. 13, 2020, in connection with Application No. PCT/US2020/042016.
International Search Report and Written Opinion, dated Dec. 10, 2020, in connection with Application No. PCT/US2020/042016.

[No Author Listed] Genbank Submission. NCBI; Accession No. WP_010869888, version WP_010869888.1. tyrosine—tRNA ligase [Methanocaldococcus jannaschii]. Jun. 1, 2019.
[No Author Listed] NCBI Accession No. XP_015843220.1. C->U editing enzyme APOBEC-1 [Peromyscus maniculatus bairdii], XP002793540.
[No Author Listed] NCBI Accession No. XP_021505673.1. C->U editing enzyme APOBEC-1 [Meriones unguiculatus], XP002793541.
Genbank Submission. NCBI; Accession No. WP_011033391, version WP_011033391.1. pyrrolysine—tRNA(Pyl) ligase [Methanosarcina mazei]. Polycarpo et al.; Nov. 29, 2019.
Genbank Submission. NCBI; Accession No. WP_011305865, version WP_011305865.1. pyrrolysine—tRNA(Pyl) ligase [Methanosarcina barkeri].Polycarpo et al.; Nov. 29, 2019.
Agarwal et al., Mode of VAMP substrate recognition and inhibition of Clostridium botulinum neurotoxin F. Nat Struct Mol Biol. Jul. 2009;16(7):789-94. doi: 10.1038/nsmb.1626. Epub Jun. 21, 2009.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Amiram et al., Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Armstrong et al., Chapter 3. Vectors for Phage Display. In: Phage Display of Peptides and Proteins. Kay et al., eds. Academic Press. San Diego, CA. 1996:35-53.
Bade et al., Botulinum neurotoxin type D enables cytosolic delivery of enzymatically active cargo proteins to neurones via unfolded translocation intermediates. J Neurochem. Dec. 2004;91(6):1461-72.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Binz et al., Clostridial neurotoxins: mechanism of SNARE cleavage and outlook on potential substrate specificity reengineering. Toxins. Apr. 2010;2(4):665-82. Epub Apr. 13, 2010.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.
Bolusani et al., Evolution of variants of yeast site-specific recombinase Flp that utilize native genomic sequences as recombination target sites. Nucleic Acids Res. 2006;34(18):5259-69. Epub Sep. 26, 2006.

(56) References Cited

OTHER PUBLICATIONS

Box et al., A multi-domain protein system based on the HC fragment of tetanus toxin for targeting DNA to neuronal cells. J Drug Target. Jul. 2003;11(6):333-43. doi: 10.1080/10611860310001634667.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Cadwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.
Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Cattaneo et al., SEL1L affects human pancreatic cancer cell cycle and invasiveness through modulation of PTEN and genes related to cell-matrix interactions. Neoplasia. 2005;7(11):1030-1038.
Chaddock et al., Inhibition of vesicular secretion in both neuronal and nonneuronal cells by a retargeted endopeptidase derivative of Clostridium botulinum neurotoxin type A. Infect. Immun. May 2000;68(5):2587-93.
Chaineau et al., Multiple roles of the vesicular-SNARE TI-VAMP in post-Golgi and endosomal trafficking. FEBS Letters. Oct. 2009;583:3817-26.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Chen, Clinical uses of botulinum neurotoxins: current indications, limitations and future developments. Toxins (Basel). 2012;4(10):913-939.
Chen et al., Engineering botulinum neurotoxin to extend therapeutic intervention. PNAS. Jun. 2009;106(23):9180-4.
Chen et al., SNARE-mediated membrane fusion. Nat Rev Mol Cell Biol. Feb. 2001;2(2):98-106.
Chen et al., VAMP8 facilitates cellular proliferation and temozolomide resistance in human glioma cells. Neuro-Oncology. 2015;17(3):407-18. Epub Sep. 10, 2014.
Chin, Expanding and reprogramming the genetic code of cells and animals. Annu Rev Biochem. 2014;83:379-408. doi: 10.1146/annurev-biochem-060713-035737. Epub Feb. 10, 2014.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Cong et al., Multiplex genome engineering using CRISPR/Cas systems. Science. 2013; 339:819-23.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Craik et al., Proteases as therapeutics. Biochem J. Apr. 2011;435(1):16 pages.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in *Escherichia coli* K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Deltcheva et al., CRISPR RNA maturation by trans-encoded small RNA and host factor RNase III. Nature. Mar. 31, 2011;471(7340):602-7. doi: 10.1038/nature09886.
Deribe, Mechanistic insights into the role of truncating PREX2 mutations in melanoma. Mol Cell Oncol. 2016;3(3):e1160174.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci USA. May 2013;110(22):9007-12.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci U S A. Aug. 15, 1991;88(16):7160-4.
Duggan et al., Inhibition of Release of Neurotransmitters from Rat Dorsal Root Ganglia by a Novel Conjugate of a Clostridium botulinum Toxin A Endopeptidase Fragment and Erythrina cristagalli Lectin. The Journal of Biological Chemistry. Sep. 2002;277(38):34846-52.
Durai et al., A bacterial one-hybrid selection system for interrogating zinc finger-DNA interactions. Comb Chem High Throughput Screen. May 2006;9(4):301-11.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.

(56) References Cited

OTHER PUBLICATIONS

Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.
Feng et al., ExoI: A new chemical inhibitor of the exocytic pathway. PNAS. May 2003;100(11):6469-74.
Ferretti et al., Complete genome sequence of an M1 strain of Streptococcus pyogenes. Proc Natl Acad Sci U S A. Apr. 10, 2001;98(8):4658-63. doi: 10.1073/pnas.071559398.
Fijalkowska et al., Mutants in the Exo I motif of Escherichia coli dnaQ: defective proofreading and inviability due to error catastrophe. Proc Natl Acad Sci U S A. Apr. 2, 1996;93(7):2856-61.
Foster et al., Re-engineering the target specificity of Clostridial neurotoxins—A route to novel therapeutics. Neurotoxicity Research. May 2006;9(2,3):101-7.
Foster et al., Targeted Secretion Inhibitors—Innovative Protein Therapeutics. Toxins. Dec. 2010;2:2795-815.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fu et al., Promises and Pitfalls of Intracellular Delivery of Proteins. Bioconjugate Chemistry. Aug. 2014;25:1602-8.
Fuchs et al., Targeting Recombinant Antibodies to the Surface of *Escherichia coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gill, Bacterial Toxins: a Table of Letal Amounts. Microbiological Reviews. Mar. 1982;46(1):86-94.
Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.
Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.
Guo et al., Polyspecific pyrrolysyl-tRNA synthetases from directed evolution. Proc Natl Acad Sci U S A. Nov. 25, 2014;111(47):16724-9. doi: 10.1073/pnas.1419737111. Epub Nov. 10, 2014.
Guzman et al., Tight regulation, modulation, and high-level expression by vectors containing the arabinose PBAD promoter. J Bacteriol. 1995;177(14):4121-4130.
Harris et al., Measurement of enzyme activity. Methods Enzymol. 2009;463:57-71.
Hart et al., Directed Evolution To Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hedstrom et al., Converting trypsin to chymotrypsin: the role of surface loops. Science. Mar. 1992;255(5049):1249-53.
Hendricks et al., The S. cerevisiae Mag1 3-methyladenine DNA glycosylase modulates susceptibility to homologous recombination. DNA Repair (Amst). 2002;1(8):645-659.
Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.
Ho et al., Recombinant botulinum neurotoxin A heavy chainbased delivery vehicles for neuronal cell targeting. Protein Engineering, Design & Selection. 2011;24(3):247-53. Epub Nov. 4, 2010.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., *Escherichia coli* one- and two-hybrid systems for the analysis and identification of protein-protein interactions. Methods. Jan. 2000;20(1):80-94.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.
Husimi et al., Cellstat—a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Jankovic et al., Direct selection and phage display of a Gram-positive secretome. Genome Biology. Dec. 13, 2007; 8(266):1-15.
Jiang et al., PylSn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.

(56) References Cited

OTHER PUBLICATIONS

Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein-DNA and protein-protein interactions. Proc Natl Acad Sci U S A. Jun. 20, 2000;97(13):7382-7.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Kim et al., DJ-1, a novel regulator of the tumor suppressor PTEN. Cancer Cell. 2005;7(3):263-273.
Kim et al., Increasing the genome-targeting scope and precision of base editing with engineered Cas9-cytidine deaminase fusions. Nature Biotechnology; Feb. 13, 2007; 35(4): 371-376.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Köhler, A yeast-based growth assay for the analysis of site-specific proteases. Nucleic Acids Res. 2003;31(4):e16. 5 pages.
Komor et al., Programmable editing of a target base in genomic DNA without double-stranded DNA cleavage. Nature. May 19, 2016;533(7603):420-4. doi: 10.1038/nature17946. Epub Apr. 20, 2016.
Kozak et al., Structural features in eukaryotic mRNAs that modulate the initiation of translation. J Biol Chem. Oct. 25, 1991;266(30):19867-70.
Kuzmine et al., Binding of the priming nucleotide in the initiation of transcription by T7 RNA polymerase. J Biol Chem. Jan. 31, 2003;278(5):2819-23. Epub Nov. 9, 2002.
Laskowska et al., IbpA and IbpB, the new heat-shock proteins, bind to endogenous *Escherichia coli* proteins aggregated intracellularly by heat shock. Biochimie. 1996;78(2):117-22.
Latimer et al., Specificity of monoclonal antibodies produced against phosphorothioate and ribo modified DNAs. Mol Immunol. Oct. 1995;32(14-15):1057-64.
Lebeda et al., The Zinc-Dependent Protease Activity of the Botulinum Neurotoxins. Toxins. May 2010;2:978-97.
Leconte et al., A population-based experimental model for protein evolution: effects of mutation rate and selection stringency on evolutionary outcomes. Biochemistry. Feb. 26, 2013; 52(8): 1490-1499.
Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.
Lincoln et al., Self-sustained replication of an RNA enzyme. Science. Feb. 27, 2009;323(5918):1229-32. Epub Jan. 8, 2009.
Lindemann et al., Evolution of bacteriophage in continuous culture: a model system to test antiviral gene therapies for the emergence of phage escape mutants. J Virol. Jun. 2002;76(11):5784-92.
Liu et al., Adding new chemistries to the genetic code. Annu Rev Biochem. 2010;79:413-44. doi: 10.1146/annurev.biochem.052308.105824.
Lu, The destructive effect of botulinum neurotoxins on the SNARE protein: SNAP-25 and synaptic membrane fusion. PeerJ. 2015;3:e1065. Published Jun. 30, 2015.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.
Lutz et al., Creating multiple-crossover DNA libraries independent of sequence identity. Proc Natl Acad Sci U S A. Sep. 25, 2001;98(20):11248-53. Epub Sep. 18, 2001.
Maeder et al., Robust, synergistic regulation of human gene expression using TALE activators. Nat Methods. Mar. 2013;10(3):243-5. doi: 10.1038/nmeth.2366. Epub Feb. 10, 2013.
Makeyev et al., Evolutionary potential of an RNA virus. J Virol. Feb. 2004;78(4):2114-20.
Mali et al., RNA-guided human genome engineering via Cas9. Science. 2013; 339:823-26.
Malmborg et al., Selective phage infection mediated by epitope expression on F pilus. J Mol Biol. Oct. 31, 1997;273(3):544-51.
Marcet-Palacios et al., Vesicle-associated membrane protein 7 (VAMP-7) is essential for target cell killing in a natural killer cell line. Biochem Biophys Res Commun. Feb. 15, 2008;366(3):617-23. doi: 10.1016/j.bbrc.2007.11.079. Epub Nov. 26, 2007.
Martin et al., Kinetic analysis of T7 RNA polymerase-promoter interactions with small synthetic promoters. Biochemistry. May 19, 1987;26(10):2690-6.
Masuyer et al., Engineered botulinum neurotoxins as new therapeutics. Annu Rev Pharmacal Toxicol. 2014;54:27-51.
Mccafferty et al., Phage antibodies: filamentous phage displaying antibody variable domains. Nature. Dec. 6, 1990;348(6301):552-4.
Mcconnell et al., Constrained peptide libraries as a tool for finding mimotopes. Gene. Dec. 30, 1994;151(1-2):115-8.
Mcnaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
Mihai et al., PTEN inhibition improves wound healing in lung epithelia through changes in cellular mechanics that enhance migration. Am J Physiol Lung Cell Mol Physiol. 2012;302(3):L287-L299.
Miller et al., A TALE nuclease architecture for efficient genome editing. Nat Biotechnol. Feb. 2011;29(2):143-8. doi:10.1038/nbt.1755. Epub Dec. 22, 2010.
Milligan et al., Oligoribonucleotide synthesis using T7 RNA polymerase and synthetic DNA templates. Nucleic Acids Res. Nov. 11, 1987;15(21):8783-98.
Mills et al., An extracellular Darwinian experiment with a self-duplicating nucleic acid molecule. Proc Natl Acad Sci U S A. Jul. 1967;58(1):217-24.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Nelson et al., Filamentous phage DNA cloning vectors: a noninfective mutant with a nonpolar deletion in gene III. Virology. Jan. 30, 1981;108(2):338-50.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.

(56) References Cited

OTHER PUBLICATIONS

O'Donoghue et al., Upgrading protein synthesis for synthetic biology. Nat Chem Biol. Oct. 2013;9(10):594-8. doi: 10.1038/nchembio.1339.

O'Maille et al., Structure-based combinatorial protein engineering (SCOPE). J Mol Biol. Aug. 23, 2002;321(4):677-91.

Oeemig et al., Solution structure of DnaE intein from Nostoc punctiforme: structural basis for the design of a new split intein suitable for site-specific chemical modification. FEBS Lett. May 6, 2009;583(9):1451-6.

Opperman et al., A model for a umuDC-dependent prokaryotic DNA damage checkpoint. Proc Natl Acad Sci U S A. Aug. 3, 1999;96(16):9218-23.

Ostendorf et al., Characterization of a dam mutant of Serratia marcescens and nucleotide sequence of the dam region. J Bacteriol. Jul. 1999;181(13):3880-5.

Ostermeier et al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pickett et al., Towards New Uses of Botulinum Toxin as a Novel Therapeutic Tool. Toxins. Jan. 2011;3:63-81.

Pogson et al., Engineering Next Generation Proteases. Curr Opin Biotechnol. Aug. 2009;20(4):390-7.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46. doi: 10.1006/jmbi.1999.2605.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Rakonjac et al., Filamentous phage are released from the bacterial membrane by a two-step mechanism involving a short C-terminal fragment of pIII. J Mol Biol. Jun. 25, 1999;289(5):1253-65.

Rakonjac et al., Filamentous phage infection-mediated gene expression: construction and propagation of the gIII deletion mutant helper phage R408d3. Gene. Oct. 1, 1997;198(1-2):99-103.

Rakonjac et al., Roles of pIII in filamentous phage assembly. J Mol Biol. Sep. 11, 1998;282(1):25-41.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rawlings et al., MEROPS: the database of proteolytic enzymes, their substrates and inhibitors. Nucleic Acids Res. Jan. 2014;42(Database issue):D503-9.

Rebar et al., Phage display methods for selecting zinc finger proteins with novel DNA-binding specificities. Methods Enzymol. 1996;267:129-49.

Reidhaar-Olson et al., Random mutagenesis of protein sequences using oligonucleotide cassettes. Methods Enzymol. 1991;208:564-86.

Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.

Riechmann et al., The C-terminal domain of TolA is the coreceptor for filamentous phage infection of *E. coli*. Cell. Jul. 25, 1997;90(2):351-60.

Ringquist et al., Translation initiation in *Escherichia coli*: sequences within the ribosome-binding site. Mol Microbiol. May 1992;6(9):1219-29.

Rosenberg et al., T7 Select® Phage Display System: A Powerful new protein display system based on bacteriophage T7. Innovations. 1996;6:1-6.

Rossetto et al., Botulinum neurotoxins: genetic, structural and mechanistic insights. Nat Rev Microbiol. Aug. 2014;12(8):535-49. doi: 10.1038/nrmicro3295. Epub Jun. 30, 2014.

Santini et al., Efficient display of an HCV cDNA expression library as C-terminal fusion to the capsid protein D of bacteriophage lambda. J Mol Biol. Sep. 11, 1998;282(1):125-35.

Santoro et al., Directed evolution of the site specificity of Cre recombinase. Proc Natl Acad Sci U S A. Apr. 2, 2002;99(7):4185-90. Epub Mar. 19, 2002.

Schultz et al., Oligo-2'-fluoro-2'-deoxynucleotide N3'—>P5' phosphoramidates: synthesis and properties. Nucleic Acids Res. Aug. 1, 1996;24(15):2966-73.

Scott et al., Searching for peptide ligands with an epitope library. Science. Jul. 27, 1990;249(4967):386-90.

Sices et al., A genetic screen for the isolation and characterization of site-specific proteases. Proc Natl Acad Sci U S A. Mar. 17, 1998;95(6):2828-33.

Sices et al., Rapid genetic selection of inhibitor-resistant protease mutants: clinically relevant and novel mutants of the HIV protease. AIDS Res Hum Retroviruses. Sep. 1, 2001;17(13):1249-55.

Sieber et al., Libraries of hybrid proteins from distantly related sequences. Nat Biotechnol. May 2001;19(5):456-60.

Sikorra et al., Substrate Recognition Mechanism of VAMP/Synaptobrevin-cleaving Clostridial Neurotoxins. Journal of Biological Chemistry. 2008;283:21145-52. Epub May 29, 2008.

Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.

Smith, Filamentous fusion phage: novel expression vectors that display cloned antigens on the virion surface. Science. Jun. 14, 1985;228(4705):1315-7.

Somm et al., A botulinum toxin—drived targeted secretion inihibitor downregulates the GH/IGF1 axis. The Journal of Clinical Investigation. Sep. 2012;122(9):3295-306.

Steffen et al., MT1-MMP-Dependent Invasion Is Regulated by TI-VAMP/VAMP7. Current Biology. Jun. 2008;18:926-31.

Stemmer, Rapid evolution of a protein in vitro by DNA shuffling. Nature. Aug. 4, 1994;370(6488):389-91.

Sutter et al., Non-replicating vaccinia vector efficiently expresses bacteriophage T7 RNA polymerase. FEBS Lett. Aug. 28, 1995;371(1):9-12.

Torres et al., Non-integrative lentivirus drives high-frequency cre-mediated cassette exchange in human cells. PLoS One. 2011;6(5):e19794. doi: 10.1371/journal.pone.0019794. Epub May 23, 2011.

Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.

Tsai et al., Targeting botulinum neurotoxin persistence by the ubiquitin-proteasome system. PNAS. Sep. 2010;107(38):16554-9.

Tsuji et al., Random multi-recombinant PCR for the construction of combinatorial protein libraries. Nucleic Acids Res. Oct. 15, 2001;29(20):E97.

Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.

Tzagoloff et al., The Initial Steps In Infection With Coliphage M13. Virology. Nov. 1964;24:372-80.

Umehara et al., N-acetyl lysyl-tRNA synthetases evolved by a CcdB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.

Varadarajan et al., Engineering of protease variants exhibiting high catalytic activity and exquisite substrate selectivity. PNAS. May 2005;102(19):6855-60.

Varadarajan et al., Highly active and selective endopeptidases with programmed substrate specificities. Nat Chem Biol. May 2008;4(5):290-4.

Vidal et al., Yeast forward and reverse 'n'-hybrid systems. Nucleic Acids Res. Feb. 15, 1999;27(4):919-29.

(56) References Cited

OTHER PUBLICATIONS

Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Continuous directed evolutions of proteins with improved soluble expression. Nature Chemical Biology. Nat Publishing Group. Aug. 20, 2018; 14(10):972-980.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.
Webb et al., Production of catalytically inactive BoNT/A1 holoprotein and comparison with BoNT/A1 subunit vaccines against toxin subtypes A1, A2, and A3. Vaccine. 2009;27(33):4490-4497.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Williams et al., SNAP23, Syntaxin4, and vesicle-associated membrane protein 7 (VAMP7) mediate trafficking of membrane type 1—matrix metalloproteinase (MT1-MMP) during invadopodium formation and tumor cell invasion. MBoC. Jul. 2014;25:2061-70.
Wright et al., Continuous in vitro evolution of catalytic function. Science. Apr. 25, 1997;276(5312):614-7.
Yamamoto et al., Virological and immunological bases for HIV-1 vaccine design. Uirusu 2007;57(2):133-139. https://doi.org/10.2222/jsv.57.133.
Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.
Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.
Yeh et al., Retargeted Clostridial neurotoxins as Novel Agents for Treating Chronic Diseases. Biochemistry. Nov. 2011;50:10419-21.
Yi et al., Engineering of TEV protease variants by yeast ER sequestration screening (YESS) of combinatorial libraries. PNAS. Apr. 2013;110(18):7229-34.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
Ziemann et al., Gene name errors are widespread in the scientific literature. Genome Biol. Aug. 23, 2016;17(1):177. doi: 10.1186/s13059-016-1044-7.
U.S. Appl. No. 13/062,098, filed Apr. 4, 2011, Liu et al.
U.S. Appl. No. 14/704,226, filed May 5, 2015, Liu et al.
U.S. Appl. No. 15/713,403, filed Sep. 22, 2017, Liu et al.
U.S. Appl. No. 13/996,208, filed Jun. 20, 2013, Liu et al.
U.S. Appl. No. 15/188,627, filed Jun. 21, 2016, Liu et al.
U.S. Appl. No. 16/410,767, filed May 13, 2019, Liu et al.
U.S. Appl. No. 14/320,519, filed Jun. 30, 2014, Liu et al.
U.S. Appl. No. 14/913,458, filed Feb. 22, 2016, Liu et al.
U.S. Appl. No. 16/266,937, filed Feb. 4, 2019, Liu et al.
U.S. Appl. No. 15/112,759, filed Jul. 20, 2016, Liu et al.
U.S. Appl. No. 16/238,386, filed Jan. 2, 2019, Liu et al.
U.S. Appl. No. 15/217,839, filed Jul. 22, 2016, Liu et al.
U.S. Appl. No. 15/518,639, filed Apr. 12, 2017, Liu et al.
U.S. Appl. No. 17/123,632, filed Dec. 16, 2020, Liu et al.
U.S. Appl. No. 15/567,312, filed Oct. 17, 2017, Liu et al.
U.S. Appl. No. 15/748,053, filed Jan. 26, 2018, Liu et al.
U.S. Appl. No. 16/804,228, filed Feb. 28, 2020, Liu et al.
U.S. Appl. No. 15/216,844, filed Jul. 22, 2016, Liu et al.
U.S. Appl. No. 16/628,456, filed Jan. 3, 2020, Liu et al.
U.S. Appl. No. 16/648,162, filed Mar. 17, 2020, Liu et al.
U.S. Appl. No. 17/251,276, filed Dec. 11, 2020, Liu et al.
U.S. Appl. No. 16/641,630, filed Feb. 24, 2020, Liu et al.
EP 09812363.1, dated Mar. 30, 2012, Extended European Search Report.
EP 16 20 3684, dated May 26, 2017, Extended European Search Report.
PCT/US2009/056194, dated Jun. 21, 2010, International Search Report and Written Opinion.
PCT/US2009/056194, dated Mar. 17, 2011, International Preliminary Report on Patentability.
EP 17 16 0955, dated May 16, 2017, Extended European Search Report.
PCT/US2011/066747, dated Aug. 30, 2012, Invitation to Pay Additional Fees.
PCT/US2011/066747, dated Oct. 30, 2012, International Search Report and Written Opinion.
PCT/US2011/066747, dated Jul. 4, 2013, International Preliminary Report on Patentability.
PCT/US2014/052231, dated Jan. 30, 2015, International Search Report and Written Opinion.
PCT/US2014/052231, dated Mar. 3, 2016, International Preliminary Report on Patentability.
PCT/US2015/012022, dated Sep. 25, 2015, International Search Report and Written Opinion.
PCT/US2015/012022, dated Aug. 4, 2016, International Preliminary Report on Patentability.
PCT/US/2016/043559, dated Jan. 12, 2017, Invitation to Pay Additional Fees.
PCT/US/2016/043559, dated Mar. 10, 2017, International Search Report and Written Opinion.
PCT/US/2016/043559, dated Feb. 1, 2018, International Preliminary Report on Patentability.
PCT/US2015/057012, dated Jun. 10, 2016, International Search Report and Written Opinion.
PCT/US2015/057012, dated May 4, 2017, International Preliminary Report on Patentability.
PCT/US2016/027795, dated Aug. 11, 2016, International Search Report and Written Opinion.
PCT/US2016/027795, dated Oct. 26, 2017, International Preliminary Report on Patentability.
PCT/US2016/044546, dated Oct. 12, 2016, Invitation to Pay Additional Fees.
PCT/US2016/044546, dated Dec. 28, 2016, International Search Report and Written Opinion.
PCT/US2016/044546, dated Feb. 8, 2018, International Preliminary Report on Patentability.
PCT/US2016/043513, dated Nov. 30, 2016, International Search Report and Written Opinion.
PCT/US2016/043513, dated Feb. 1, 2018, International Preliminary Report on Patentability.
PCT/US2018/14867, dated Apr. 5, 2018, Invitation to Pay Additional Fees.
PCT/US2018/14867, dated May 23, 2018, International Search Report and Written Opinion.
PCT/US2018/14867, dated Aug. 1, 2019, International Preliminary Report on Patentability.
PCT/US2018/040692, dated Sep. 12, 2018, International Search Report and Written Opinion.
PCT/US2018/040692, dated Nov. 15, 2018, International Search Report and Written Opinion.
PCT/US2018/040692, dated Jan. 16, 2020, International Preliminary Report on Patentability.

(56) References Cited

OTHER PUBLICATIONS

PCT/US2018/051557, dated Jan. 4, 2019, Invitation to Pay Additional Fees.
PCT/US2018/051557, dated Feb. 25, 2019, International Search Report and Written Opinion.
PCT/US2018/051557, dated Apr. 2, 2020, International Preliminary Report on Patentability.
PCT/US2018/044242, dated Nov. 21, 2018, International Search Report and Written Opinion.
PCT/US2019/037216, dated Sep. 4, 2019, International Search Report and Written Opinion.
PCT/US2019/037216, dated Dec. 24, 2020, International Preliminary Report on Patentability.
PCT/US18/481134, dated Nov. 19, 2018, Invitation to Pay Additional Fees.
PCT/US18/481134, dated Jan. 22, 2019, International Search Report and Written Opinion.
PCT/US18/481134, dated Mar. 5, 2020, International Preliminary Report on Patentability.
PCT/US2020/042016, dated Oct. 13, 2020, Invitation to Pay Additional Fees.
PCT/US2020/042016, dated Dec. 10, 2020, International Search Report and Written Opinion.

```
RosaLoxP    ABCDEFGHIJKLM    12345678    MLKJIHGFEDCBA
'invRosa'   ABCDEFGHIJKLM    87654321    MLKJIHGFEDCBA
```

Carlson, J.C. et al. 2014. *Nat. Chem. Biol.* 10, 216–222.

Oligos: wt loxP
Cre: from NEB

Oligos: attB, attP
BxB1: from NEB PureExpress

SEQ ID NO: 2 LoxP  ATAACTTCG T A T AGCATACAT T A T ACGAAGTTAT
SEQ ID NO: 4 Rosa  ATCTCATGG T T T ATGCTAAAC T A T ATGTTGACAT SEQ ID NO: 2 LoxP ATAACTTCG T A T AGCATACAT T A T ACGAAGTTAT
SEQ ID NO: 4 Rosa ATCTCATGG T T T ATGCTAAAC T A T ATGTTGACAT

SEQUENCE LISTING

<160> NUMBER OF SEQ ID NOS: 13

<210> SEQ ID NO 1
<211> LENGTH: 343
<212> TYPE: PRT
<213> ORGANISM: Artificial Sequence
<220> FEATURE:
<223> OTHER INFORMATION: Synthetic Polypeptide

<400> SEQUENCE: 1

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

```
<210> SEQ ID NO 2
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 2
ataacttcgt atagcataca ttatacgaag ttat                              34

<210> SEQ ID NO 3
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 3
gaagttccta ttctctagaa agtataggaa cttc                              34

<210> SEQ ID NO 4
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 4
atctcatggt ttatgctaaa ctatatgttg acat                              34

<210> SEQ ID NO 5
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 5
atcacttggt atagcataaa ttataccaag tgat                              34

<210> SEQ ID NO 6
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 6
atcacttggt ttatcctaaa ttaaaccaag tgat                              34

<210> SEQ ID NO 7
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 7
atctcttggt ttatcctaaa ctaaaccaag agat                              34

<210> SEQ ID NO 8
<211> LENGTH: 34
<212> TYPE: DNA
<213> ORGANISM: Artificial Sequence
<220> FEATURE:
<223> OTHER INFORMATION: Synthetic Polynucleotide
```

```
<400> SEQUENCE: 8
atctcatggt ttatgctaaa ctaaaccatg agat                                  34

<210> SEQ ID NO 9
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 9
atatcttcat atagcataaa ttatatgaag atat                                  34

<210> SEQ ID NO 10
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 10
atgtcttcat atatcctaaa ttatatgaag acat                                  34

<210> SEQ ID NO 11
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 11
atgtctacat atatcctaaa ctatatgtag acat                                  34

<210> SEQ ID NO 12
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 12
atgtcaacat atatgctaaa ctatatgttg acat                                  34

<210> SEQ ID NO 13
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 13
nnnnnngcnn ataacttcgt atagcataca ttatacgaag ttatnn                     46
```

US 11,104,967 B2

EVOLUTION OF SITE-SPECIFIC RECOMBINASES

RELATED APPLICATIONS

This application is a divisional of and claims priority under 35 U.S.C. § 120 to U.S. patent application, U.S. Ser. No. 15/216,844, filed Jul. 22, 2016, entitled "EVOLUTION OF SITE-SPECIFIC RECOMBINASES," which claims priority under 35 U.S.C. § 119(e) to U.S. provisional application, U.S. Ser. No. 62/195,739, filed on Jul. 22, 2015, entitled "EVOLUTION OF SITE-SPECIFIC RECOMBINASES," each of which is incorporated herein by reference.

FEDERALLY SPONSORED RESEARCH

This invention was made with government support under grant numbers HR0011-11-2-0003 and N66001-12-C-4207 awarded by the Department of Defense. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Nov. 14, 2019, is named H082470219US02-SEQ and is 5 kilobytes in size.

BACKGROUND

Targeted genetic engineering of cells and organisms holds great promise for research and therapy. While some tools for site-specific modifications of genomic sequences have been developed, such as, for example, site-specific nucleases or nickases that can introduce double-stranded or single-stranded cuts in a genomic target sequence, the targeted integration, deletion, or inversion of sequences within a genome relies on relatively ineffective technologies, such as homologous recombination and gene targeting. Methods and molecular tools for direct manipulation of a target sequence within a genome are therefore highly desirable.

SUMMARY

The ability to precisely modify the genome of human cells has enormous potential as a novel therapy and a powerful research tool. Programmable nucleases, such as zinc finger nucleases (ZFNs), transcriptional activator-like effector nucleases (TALENs) or Cas9, can specifically cleave DNA at a target sequence, but they rely on stochastic host cells processes to effect gene insertion or other genome modifications. In contrast, site specific recombinases directly catalyze genomic recombination at a target sequence with high specificity and efficiency. Recombinases can be used, for example, to effect insertions, deletions, and inversions of nucleic acid sequences at a specific target sequence. In some embodiments, recombinases can also be used to exchange nucleic acid sequences, e.g., in the context of replacing a sequence associated with a disease or disorder with a sequence not associated with a disease or disorder.

A major limitation of using recombinases for effecting targeted genomic modifications is that recombinases, such as serine or tyrosine recombinases (e.g., Cre recombinase; λ phage integrase; FLP recombinase; phiC31 integrase; Dre recombinase; BxB 1; Hin; and prokaryotic β-recombinase), typically bind relatively complex DNA target sequences (e.g., LoxP sites in the case of Cre recombinase or FRT sites in the case of FLP recombinases) with high specificity. Target cells lacking the required recombinase target sequence within their genome can thus not be efficiently modified. For example, mouse and human cells typically lack recombinase target sequences within their genome and can thus not be easily modified using recombinases. While it is possible to introduce a native recombinase target sequence (e.g., a wild-type LoxP or FRT site) into a desired genetic locus within a cell's genome, and thus render the cell suitable for modification with a native recombinase, the introduction of such recombinase target sequences typically requires time- and labor-intensive gene targeting strategies.

Some aspects of this disclosure are based on the surprising discovery that recombinases can be evolved to recognize non-native DNA target sequences via directed evolution methods, e.g., by the phage-assisted continuous evolution (PACE) strategies and methods disclosed herein. For an overview of PACE technology, see, for example, International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. Application, U.S. Ser. No. 13/922,812, filed Jun. 20, 2013, the entire contents of each of which are incorporated herein by reference. Using the evolution strategies and methods provided herein, recombinases can be adapted to target virtually any desired sequence, e.g., any locus within the genome of a cell. This allows, for example, for the introduction of recombinant sequences into the genome of a desired target cell without the need for inserting a recombinase target sequence first. In addition, the evolved recombinases can also be used to remove, invert, or replace nucleic acid sequences from a target sequence, e.g., from a genomic sequence in a cell or subject.

Some aspects of this disclosure provide methods for evolving recombinases. In some embodiments, the methods comprise (a) contacting a population of host cells with a population of phage vectors comprising a gene encoding a recombinase and deficient in at least one gene for the generation of infectious phage particles, wherein (1) the host cells are amenable to transfer of the phage vector; (2) the vector allows for expression of the recombinase in a host cell, can be replicated by the host cell, and the replicated vector can transfer from host cell to host cell; (3) the host cells express a gene product encoded by the at least one gene for the generation of infectious phage particles of (a) in response to the recombination of a recombinase target sequence by the recombinase, and the level of gene product expression depends on the activity of the recombinase towards the target sequence; (b) incubating the population of host cells under conditions allowing for mutation of the gene encoding the recombinase and the transfer of the phage vectors from host cell to host cell, wherein host cells are removed from the host cell population, and the population of host cells is replenished with fresh host cells that do not harbor the phage vector; and (c) isolating a replicated phage vector from the host cell population in (b), wherein the replicated vector comprises a mutated version of the gene encoding the recombinase.

Some aspects of this disclosure provide evolved recombinases comprising an amino acid sequence that is at least 70%, at least 80%, at least 90%, at least 95%, or at least 97% identical to the sequence of a wild-type recombinase, wherein the amino acid sequence of the evolved recombinase comprises at least one mutation as compared to the sequence of the wild-type recombinase, and wherein the evolved recombinase recognizes a DNA recombinase target sequence that differs from the canonical recombinase target sequence by at least one nucleotide. In some embodiments, In some embodiments, the evolved recombinase recognizes a DNA recombinase target sequence that differs from the canonical recombinase target sequence by at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 at least 25, or at least 30 nucleotides. In some embodiments, the evolved recombinase recognizes a DNA recombinase target sequence that differs from the canonical recombinase target sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

Some aspects of this disclosure provide methods for engineering a nucleic acid molecule, the method comprising contacting a first nucleic acid molecule comprising a first recombinase target sequence of the structure 5'-[left half-site]-[spacer]-[right half-site]-3' with a recombinase and a second nucleic acid molecule comprising a second recombinase target sequence under conditions suitable for the recombinase to bind and recombine the recombinase target sequences, wherein the first and the second recombinase target sequences differ from the canonical Cre recombinase target sequence 5'-ATAACTTCGTATA GCATACAT TATACGAAGTTAT-3' (LoxP, SEQ ID NO: 2) in at least 1, at least 2, at least 3, at least 4, at least 5, at least 6, at least 7, at least 8, at least 9, at least 10, at least 11, at least 12, at least 13, at least 14, or at least 15 nucleotides.

Some aspects of this disclosure provide methods for identifying a target site of a recombinase. In some embodiments, the comprises (a) providing a recombinase that binds and recombines a double-stranded nucleic acid target sequence of the structure 5'-[left half-site]-[spacer]-[right half-site]-3; (b) contacting the recombinase of (a) with a library of candidate nucleic acid molecules, wherein each candidate nucleic acid molecule comprises a nucleic acid strand comprising the structure 5'-[spacer]-[half-site]-[loop sequence]-[half-site]-[spacer]-3', wherein the spacer and half-site sequences on the 5' and 3' end are complementary and hybridize to each other, thus forming a single-stranded loop structure and a double-stranded [half-site]-[spacer] structure, and wherein each candidate nucleic acid molecule comprises a PCR primer binding site within the loop sequence, under conditions suitable for the recombinase to bind a candidate nucleic acid molecule comprising a [spacer]-[half-site]-structure and recombine it with the [spacer]-[half-site] structure of a different candidate nucleic acid molecule, thus creating a recombined circular nucleic acid molecule comprising a [loop sequence]-[half-site]-[spacer]-[half-site]-[loop sequence] structure; and (c) identifying recombinase target sites bound and recombined by the recombinase in (b) by determining the sequence of the [half-site]-[spacer]-[half-site] structure of the recombined circular nucleic acid molecule in (b).

Some aspects of this disclosure provide libraries of nucleic acid molecules that are useful for assessing the target sites preferences of recombinases. In some embodiments the library comprises a plurality of nucleic acid molecules, wherein each nucleic acid molecule comprises a 5'-[spacer]-[half-site]-[loop sequence]-[half-site]-[spacer]-3' structure, wherein the spacer and half-site sequences on the 5' and 3' end are complementary and hybridize to each other, thus forming a single-stranded loop structure and a double-stranded [half-site]-[spacer] structure, and wherein each candidate nucleic acid molecule comprises a PCR primer binding site within the loop sequence.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, Drawings, Examples, and Claims.

DEFINITIONS

Figure 1:
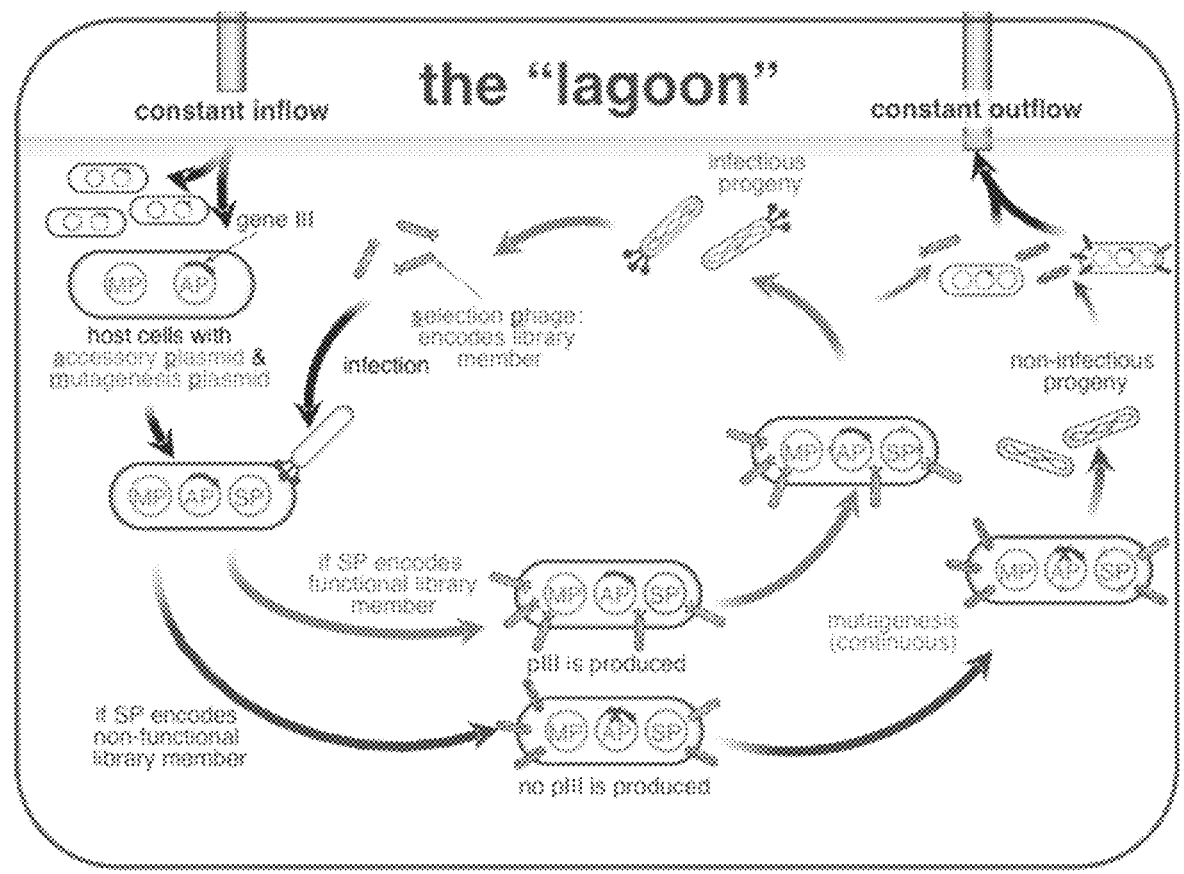
FIG. 1. Schematic illustration of an exemplary embodiment of Phage-Assisted Continuous Evolution (PACE).

The term "accessory plasmid," as used herein, refers to a plasmid comprising a gene required for the generation of infectious viral particles under the control of a conditional promoter. In the context of continuous evolution of recombinases described herein, transcription from the conditional promoter of the accessory plasmid is typically activated by a function of the recombinase to be evolved. Accordingly, the accessory plasmid serves the function of conveying a competitive advantage to those viral vectors in a given population of viral vectors that carry a gene of interest able to activate the conditional promoter. Only viral vectors carrying an "activating" version of the recombinase of interest will be able to induce expression of the gene required to generate infectious viral particles in the host cell, and, thus, allow for packaging of infectious viral particles and propagation of the viral genome in the flow of host cells. Vectors carrying non-activating versions of the recombinase of interest, on the other hand, will not induce expression of the gene required to generate infectious viral vectors, and, thus, will not be packaged into viral particles that can infect fresh host cells.

The term "cellstat," as used herein, refers to a culture vessel comprising host cells, in which the number of cells is substantially constant over time.

The term "continuous evolution," as used herein, refers to an evolution process, in which a population of nucleic acids encoding a recombinase of interest is subjected to multiple rounds of (a) replication, (b) mutation, and (c) selection to produce a desired evolved recombinase that is different from the original recombinase of interest, for example, in that it binds and recombines a target site not recognized by the original recombinase, or in that it binds and recombines a target site with higher affinity or efficiency than the original recombinase. The multiple rounds can be performed without investigator intervention, and the steps (a)-(c) can be carried out simultaneously. Typically, the evolution procedure is carried out in vitro, for example, using cells in culture as host cells. In general, a continuous evolution process provided herein relies on a system in which a gene encoding a recombinase of interest is provided in a viral vector that undergoes a life-cycle including replication in a host cell and transfer to another host cell, wherein a critical component of the life-cycle, e.g., a gene essential for the generation of infectious viral particles, is deactivated and reactivation of the component is dependent upon an activity of the recombinase of interest that is a result of a mutation in the viral vector.

The term "flow", as used herein in the context of host cells, refers to a stream of host cells, wherein fresh host cells not harboring the transfer vector (e.g., the viral vector encoding the recombinase of interest) are being introduced into a host cell population, for example, a host cell population in a lagoon, remain within the population for a limited time, and are then removed from the host cell population. In a simple form, a host cell flow may be a flow through a tube, or a channel, for example, at a controlled rate. In other embodiments, a flow of host cells is directed through a lagoon that holds a volume of cell culture media and comprises an inflow and an outflow. The introduction of fresh host cells may be continuous or intermittent and removal may be passive, e.g., by overflow, or active, e.g., by active siphoning or pumping. Removal further may be random, for example, if a stirred suspension culture of host cells is provided, removed liquid culture media will contain freshly introduced host cells as well as cells that have been a member of the host cell population within the lagoon for some time. Even though, in theory, a cell could escape removal from the lagoon indefinitely, the average host cell will remain only for a limited period of time within the lagoon, which is determined mainly by the flow rate of the culture media (and suspended cells) through the lagoon. Since the viral vectors replicate in a flow of host cells, in which fresh, uninfected host cells are provided while infected cells are removed, multiple consecutive viral life cycles can occur without investigator interaction, which allows for the accumulation of multiple advantageous mutations in a single evolution experiment.

The term "fresh," as used herein in the context of host cells, and used interchangeably with the terms "non-infected" or "uninfected" in the context of host cells of viral vectors, refers to a host cell that does not harbor the vector or, in the context of viral vectors, has not been infected by the viral vector comprising a gene encoding a recombinase of interest as used in a continuous evolution process provided herein. A fresh host cell can, however, have been infected by a viral vector unrelated to the vector to be evolved or by a vector of the same or a similar type but not carrying the gene of interest.

The term "gene of interest" or "gene encoding a recombinase of interest," as used herein, refers to a nucleic acid construct comprising a nucleotide sequence encoding a gene product, e.g., a recombinase, of interest to be evolved in a continuous evolution process as provided herein. The term includes any variations of a gene of interest that are the result of a continuous evolution process according to methods provided herein. For example, in some embodiments, a gene of interest is a nucleic acid construct comprising a nucleotide sequence encoding a recombinase to be evolved, cloned into a viral vector, for example, a phage genome, so that the expression of the encoding sequence is under the control of one or more promoters in the viral genome. In other embodiments, a gene of interest is a nucleic acid construct comprising a nucleotide sequence encoding a recombinase to be evolved and a promoter operably linked to the encoding sequence. When cloned into a viral vector, for example, a phage genome, the expression of the encoding sequence of such genes of interest is under the control of the heterologous promoter and, in some embodiments, may also be influenced by one or more promoters comprised in the viral genome.

The term "helper phage," as used herein interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes for the generation of infectious phage particles. Helper phages are useful to allow modified phages that lack a gene for the generation of infectious phage particles to complete the phage life cycle in a host cell. Typically, a helper phage will comprise the genes for the generation of infectious phage particles that are lacking in the phage genome, thus complementing the phage genome. In the continuous evolution context, the helper phage typically complements the selection phage, but both lack a phage gene required for the production of infectious phage particles.

The terms "high copy number plasmid" and "low copy number plasmid" are art-recognized, and those of skill in the art will be able to ascertain whether a given plasmid is a high or low copy number plasmid. In some embodiments, a low copy number accessory plasmid is a plasmid exhibiting an average copy number of plasmid per host cell in a host cell population of about 5 to about 100. In some embodiments, a very low copy number accessory plasmid is a plasmid exhibiting an average copy number of plasmid per host cell in a host cell population of about 1 to about 10. In some embodiments, a very low copy number accessory plasmid is a single-copy per cell plasmid. In some embodiments, a high copy number accessory plasmid is a plasmid exhibiting an average copy number of plasmid per host cell in a host cell population of about 100 to about 5000.

The term "host cell," as used herein, refers to a cell that can host, replicate, and transfer a phage vector useful for a continuous evolution process as provided herein. In embodiments where the vector is a viral vector, a suitable host cell is a cell that can be infected by the viral vector, can replicate it, and can package it into viral particles that can infect fresh host cells. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the disclosure is not limited in this respect.

The term "infectious viral particle," as used herein, refers to a viral particle able to transport the viral genome it comprises into a suitable host cell. Not all viral particles are able to transfer the viral genome to a suitable host cell. Particles unable to accomplish this are referred to as non-infectious viral particles. In some embodiments, a viral particle comprises a plurality of different coat proteins, wherein one or some of the coat proteins can be omitted without compromising the structure of the viral particle. In some embodiments, a viral particle is provided in which at least one coat protein cannot be omitted without the loss of infectivity. If a viral particle lacks a protein that confers infectivity, the viral particle is not infectious. For example, an M13 phage particle that comprises a phage genome packaged in a coat of phage proteins (e.g., pVIII) but lacks pIII (protein III) is a non-infectious M13 phage particle because pIII is essential for the infectious properties of M13 phage particles.

The term "lagoon," as used herein, refers to a culture vessel or bioreactor through which a flow of host cells is directed. When used for a continuous evolution process as provided herein, a lagoon typically holds a population of host cells and a population of viral vectors replicating within the host cell population, wherein the lagoon comprises an outflow through which host cells are removed from the lagoon and an inflow through which fresh host cells are introduced into the lagoon, thus replenishing the host cell population.

The term "mutagen," as used herein, refers to an agent that induces mutations or increases the rate of mutation in a given biological system, for example, a host cell, to a level above the naturally occurring level of mutation in that system. Some exemplary mutagens useful for continuous evolution procedures are provided elsewhere herein, and other useful mutagens will be evident to those of skill in the art. Useful mutagens include, but are not limited to, ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene,3-Chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9), and t-butyl hydroperoxide (BHP) (CAS no. 75-91-2). Additional mutagens can be used in continuous evolution procedures as provided herein, and the invention is not limited in this respect.

The term "mutagenesis plasmid," as used herein, refers to a plasmid comprising a nucleic acid sequence encoding a gene product or a combination of gene products that act(s) as a mutagen. In some embodiments, a mutagenesis plasmid may encode a DNA polymerase lacking a proofreading capability. In some embodiments, the mutagenesis plasmid may encode a gene product involved in the bacterial SOS stress response, for example, a component of a bacterial translesion synthesis polymerase V. In some embodiments, the mutagenesis plasmid may encode a deoxyadenosine methylase. In some embodiments, the mutagenesis plasmid may encode a hemimethylated-GATC binding domain. In some non-limiting embodiments, the mutagenesis plasmid encodes UmuC (a component of E. coli translesion synthesis polymerase V), dam (deoxyadenosine methylase), and/or seqA (hemimethylated-GATC binding domain), or any combination thereof.

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, P1, P2, P4, Phi X174, N4, Φ6, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1$^{st}$ edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1$^{st}$ edition (December 2008), ISBN: 1603275649; all of which are incorporated herein in their entirety by reference for disclosure of suitable phages and host cells as well as methods and protocols for isolation, culture, and manipulation of such phages).

The term "phage-assisted continuous evolution (PACE)," as used herein, refers to continuous evolution that employs phage as viral vectors. PACE technology has been described previously, for example, in International PCT Application, PCT/US2009/056194, filed Sep. 8, 2009, published as WO 2010/028347 on Mar. 11, 2010; International PCT Application, PCT/US2011/066524, filed Dec. 22, 2011, published as WO 2012/088381 on Jun. 28, 2012; and U.S. Application, U.S. Ser. No. 13/922,812, filed Jun. 20, 2013, each of which is incorporated herein by reference.

The term "promoter" is art-recognized and refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active in the presence of a specific condition. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

The term "protein," as used herein refers to a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain; see, for example, cco.caltech. edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "replication product," as used herein, refers to a nucleic acid that is the result of viral genome replication by a host cell. This includes any viral genomes synthesized by the host cell from a viral genome inserted into the host cell. The term includes non-mutated as well as mutated replication products.

The term "selection phage," as used herein interchangeably with the term "selection plasmid," refers to a modified phage that comprises a gene of interest to be evolved and lacks a full-length gene encoding a protein required for the generation of infectious phage particles. For example, some M13 selection phages provided herein comprise a nucleic acid sequence encoding a recombinase to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a recombinase to be evolved, e.g., under the control of an M13 promoter, and lack all or part of a gene encoding a protein required for the generation of infective phage particles, e.g., the gIII gene encoding the pIII protein.

The terms "small molecule" and "organic compound" are used interchangeably herein and refer to molecules, whether naturally-occurring or artificially created (e.g., via chemical synthesis) that have a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, organic compounds are monomeric and have a molecular weight of less than about 1500 g/mol. In certain embodiments, the molecular weight of the small molecule is less than about 1000 g/mol or less than about 500 g/mol. In certain embodiments, the small molecule is a therapeutic drug or drug candidate, for example, a drug or drug candidate that is in clinical or pre-clinical trials or that has already been deemed safe and effective for use in humans or animals by the appropriate governmental agency or regulatory body.

The term "turbidostat," as used herein, refers to a culture vessel comprising host cells in suspension culture, in which the turbidity of the culture medium is substantially essentially constant over time. In some embodiments, the turbidity of a suspension culture, for example, of bacterial cells, is a measure for the cell density in the culture medium. In some embodiments, a turbidostat comprises an inflow of fresh media and an outflow, and a controller that regulates the flow into and/or out of the turbidostat based on the turbidity of the suspension culture in the turbidostat.

The term "vector," as used herein, refers to a nucleic acid that can be modified to encode a recombinase of interest and that is able to enter into a host cell, mutate and replicate within the host cell, and then transfer a replicated form of the vector into another host cell. Exemplary suitable vectors include viral vectors, such as retroviral vectors or bacteriophages, and conjugative plasmids. Additional suitable vectors will be apparent to those of skill in the art based on the instant disclosure.

The term "viral life cycle," as used herein, refers to the viral reproduction cycle comprising insertion of the viral genome into a host cell, replication of the viral genome in the host cell, and packaging of a replication product of the viral genome into a viral particle by the host cell.

The term "viral particle," as used herein, refers to a viral genome, for example, a DNA or RNA genome, that is associated with a coat of a viral protein or proteins, and, in some cases, with an envelope of lipids. For example, a phage particle comprises a phage genome packaged into a protein encoded by the wild type phage genome.

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene encoding the recombinase of interest to be evolved.

DETAILED DESCRIPTION

Some aspects of this disclosure provide selection strategies that can be used in PACE experiments to evolve recombinases with regard to recombinase towards a non-canonical recombinase target sequence. This technology can be used, for example, to evolve recombinases that can bind and recombine non-canonical sequences that are naturally occurring, such as, for example, sequences within a "safe harbor" genomic locus in a mammalian genome, e.g., a genomic locus that is known to be tolerant to genetic modification without any undesired effects. Recombinases targeting such sequences allow, e.g., for the targeted insertion of nucleic acid constructs at a specific genomic location without the need for conventional time- and labor-intensive gene targeting procedures, e.g., via homologous recombination technology. In addition, the directed evolution strategies provided herein can be used to evolve recombinases with an altered activity profile, e.g., recombinases that favor integration of a nucleic acid sequence over excision of that sequence or vice versa.

Some aspects of this disclosure provide methods and reagents for assessing the specificity of recombinases, for example, of naturally occurring or evolved recombinases. Libraries of nucleic acid molecules comprising candidate recombinase target half-sites are provided as well as methods of using such libraries for target sequences that are bound and recombined by a recombinase.

The directed evolution strategies provided herein can be applied to any recombinase. Recombinases are well known to those of skill in the art, and suitable recombinases that can be evolved by the methods and strategies provided herein will be apparent to the skilled artisan based on the present disclosure and the knowledge of recombinases in the art. Suitable recombinases include, for example, and without limitation, tyrosine recombinases and serine recombinases. Some exemplary suitable recombinases that can be evolved by the methods and strategies provided herein include, for example, and without limitation, Cre recombinase from bacteriophage P1 (acting on LoxP sites); λ phage integrase (acting on att sites); FLP recombinases of fungal origin (acting on FTR sites); phiC31 integrase; Dre recombinase, BxB 1; and prokaryotic β-recombinase. Additional suitable recombinases will be apparent to those of skill in the art, and such suitable recombinases include, without limitation, those disclosed in Hirano et al., Site-specific recombinases as tools for heterologous gene integration. Appl Microbiol Biotechnol. 2011 October; 92(2):227-39; Fogg et al., New applications for phage integrases. J Mol Biol. 2014 Jul. 29; 426(15):2703; Brown et al., Serine recombinases as tools for genome engineering. Methods. 2011 April; 53(4):372-9; Smith et al., Site-specific recombination by phiC31 integrase and other large serine recombinases. Biochem Soc Trans. 2010 April; 38(2):388-94; Grindley et al., Mechanisms of site-specific recombination. Annu Rev Biochem. 2006; 75:567-605; Smith et al., Diversity in the serine recombinases. Mol Microbiol. 2002 April; 44(2):299-307; Grainge et al., The integrase family of recombinase: organization and function of the active site. Mol Microbiol. 1999 August; 33(3):449-56; Gopaul et al., Structure and mechanism in site-specific recombination. Curr Opin Struct Biol. 1999 February; 9(1):14-20; Cox et al., Conditional gene expression in the mouse inner ear using Cre-loxP. J Assoc Res Otolaryngol. 2012 June; 13(3):295-322; Birling et al., Site-specific recombinases for manipulation of the mouse genome. Methods Mol Biol. 2009; 561:245-63; and Mishina M, Sakimura K. Conditional gene targeting on the pure C57BL/6 genetic background. Neurosci Res. 2007 June; 58(2):105-12; the entire contents of each of which are incorporated herein by reference.

The evolved recombinases provided herein that exhibit altered target sequence preferences as compared to their wild type counterparts, can be used to target virtually any target sequence for recombinase activity. Accordingly, the presently described evolution methods and strategies and the evolved recombinases obtained via these strategies and methods can be used to modify, for example, any sequence within the genome of a cell or subject. Because recombinases can effect an insertion of a heterologous nucleic acid molecule into a target nucleic acid molecule, an excision of a nucleic acid sequence from a nucleic acid molecule, an inversion, or a replacement of nucleic acid sequences, the technology provided herein enables the efficient modification of genomic targets in a variety of ways (e.g., integration, deletion, inversion, exchange of nucleic acid sequences).

One application of the recombinase technology provided herein is the integration of a heterologous nucleic acid sequence into a safe harbor locus in the genome of a cell. A safe harbor locus is typically a genomic locus where transgenes can integrate and function in a predictable manner without perturbing endogenous gene activity. Some exemplary safe harbor loci in the human genome include, without limitation the Rosa26 locus, the AAVS1 locus, and the safe harbor loci listed in Sadelain et al., Safe harbours for the integration of new DNA in the human genome. Nat Rev Cancer. 2011 Dec. 1; 12(1):51-8, the entire contents of which are incorporated herein by reference. Safe harbor loci in other species are also well known, including in mammals (mouse, rat, hamster, other non-human primates) and in plants, such as cash crops that are currently made transgenic by other means.

Another application of the recombinase technology provided herein is the recombinase-mediated excision or deletion of a sequence from the genome of a cell or a subject that are associated with a disease or disorder, or the exchange of one nucleotide sequence for another.

Additional applications and uses of the recombinase technology provided herein will be apparent to the skilled artisan based on the present disclosure.

Phage-Assisted Continuous Evolution

Phage-assisted continuous evolution (PACE), allows proteins and other gene products to undergo directed evolution at a rate ~100-fold faster than conventional methods. FIG. 1 provides a schematic overview of an exemplary embodiment of PACE. During PACE, an evolving population of filamentous bacteriophages ("selection phage", SP) is continuously diluted in a flow of host cells through a fixed-volume vessel (a "lagoon"). The flow rate of host cells through the lagoon results in an average time of hosts cells within the lagoon that is too short for host cell division, but longer than the average phage replication cycle, thus allowing only the phage to propagate and accumulate mutations.

Typically, each SP carries an evolving gene, for example, a gene encoding a recombinase, and lacks at least one phage gene that is essential for the generation of infectious phage particles, e.g., gene III in M13 phages. The host cells typically provide the phage gene lacking from the SP on an accessory plasmid (AP) that expresses the phage gene lacking from the SP in response to a desired activity of the evolving gene (e.g., a desired recombinase activity). As a result, only SP encoding variants of the evolving gene product having the desired activity are able to generate infectious progeny and propagate to other cells, while SP encoding inactive variants produce non-infectious progeny that cannot infect new host cells and are thus diluted out of the lagoon. PACE has been used to rapidly evolve RNA polymerases and proteases with tailor-made properties. It was tested whether the PACE system could be adapted to evolve DNA-binding domains with altered or improved DNA-binding specificity.

In some embodiments, the SP phage is a filamentous phage or phagemid. In some embodiments, the phage is an M13 phage. M13 phages are well known to those in the art and the biology of M13 phages has extensively been studied. Wild type M13 phage particles comprise a circular, single-stranded genome of approximately 6.4 kb. The wilt-type genome includes ten genes, gI-gX, which, in turn, encode the ten M13 proteins, pI-pX, respectively. gVIII encodes pVIII, also often referred to as the major structural protein of the phage particles, while gIII encodes pIII, also referred to as the minor coat protein, which is required for infectivity of M13 phage particles.

The M13 life cycle includes attachment of the phage to the sex pilus of a suitable bacterial host cell via the pIII protein and insertion of the phage genome into the host cell. The circular, single-stranded phage genome is then converted to a circular, double-stranded DNA, also termed the replicative form (RF), from which phage gene transcription is initiated. The wild type M13 genome comprises nine promoters and two transcriptional terminators as well as an origin of replication. This series of promoters provides a gradient of transcription such that the genes nearest the two transcriptional terminators (gVIII and IV) are transcribed at the highest levels. In wild-type M13 phage, transcription of all 10 genes proceeds in same direction. One of the phage-encode proteins, pII, initiates the generation of linear, single-stranded phage genomes in the host cells, which are subsequently circularized, and bound and stabilized by pV. The circularized, single-stranded M13 genomes are then bound by pVIII, while pV is stripped off the genome, which initiates the packaging process. At the end of the packaging process, multiple copies of pIII are attached to wild-type M13 particles, thus generating infectious phage ready to infect another host cell and concluding the life cycle.

The M13 phage genome can be manipulated, for example, by deleting one or more of the wild type genes, and/or inserting a heterologous nucleic acid construct into the genome. M13 does not have stringent genome size restrictions, and insertions of up to 42 kb have been reported. This allows M13 phage vectors to be used in continuous evolution experiments to evolve genes of interest without imposing a limitation on the length of the gene to be involved.

In some embodiments, the host cells comprise an accessory plasmid that drives expression of a gene essential for the generation of infectious viral particles from a conditional promoter. In some embodiments, the conditional promoter of the accessory plasmid is a promoter the transcriptional activity of which can be regulated over a wide range, for example, over 2, 3, 4, 5, 6, 7, 8, 9, or 10 orders of magnitude by the activating function, for example, function of a protein encoded by the gene of interest. In some embodiments, the level of transcriptional activity of the conditional promoter depends directly on the desired function of the gene of interest. This allows for starting a continuous evolution process with a viral vector population comprising versions of the gene of interest that only effect minimal activation of the conditional promoter. In the process of continuous evolution, any mutation in the gene of interest that increases activity of the conditional promoter directly translates into higher expression levels of the gene required for the generation of infectious viral particles, and, thus, into a competitive advantage over other viral vectors carrying minimally active or loss-of-function versions of the gene of interest.

The stringency of selective pressure imposed by the accessory plasmid in a continuous evolution procedure as provided herein can be modulated. In some embodiments, the use of low copy number accessory plasmids results in an elevated stringency of selection for versions of the gene of interest that activate the conditional promoter on the accessory plasmid, while the use of high copy number accessory plasmids results in a lower stringency of selection. The terms "high copy number plasmid" and "low copy number plasmid" are art-recognized and those of skill in the art will be able to ascertain whether a given plasmid is a high or low copy number plasmid. In some embodiments, a low copy number accessory plasmid is a plasmid exhibiting an average copy number of plasmid per host cell in a host cell population of about 5 to about 100. In some embodiments, a very low copy number accessory plasmid is a plasmid exhibiting an average copy number of plasmid per host cell in a host cell population of about 1 to about 10. In some embodiments, a very low copy number accessory plasmid is a single-copy per cell plasmid. In some embodiments, a high copy number accessory plasmid is a plasmid exhibiting an average copy number of plasmid per host cell in a host cell population of about 100 to about 5000. The copy number of an accessory plasmid will depend to a large part on the origin of replication employed. Those of skill in the art will be able to determine suitable origins of replication in order to achieve a desired copy number.

It should be understood that the function of the accessory plasmid, namely to provide a gene required for the generation of viral particles under the control of a conditional promoter the activity of which depends on a function of the gene of interest, can be conferred to a host cell in alternative ways. Such alternatives include, but are not limited to, permanent insertion of a gene construct comprising the conditional promoter and the respective gene into the genome of the host cell, or introducing it into the host cell using an different vector, for example, a phagemid, a cosmid, a phage, a virus, or an artificial chromosome. Additional ways to confer accessory plasmid function to host cells will be evident to those of skill in the art, and the invention is not limited in this respect.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector. In some embodiments, the viral vector is a phage and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect.

In some embodiments, the host cell is an *E. coli* cell. In some PACE embodiments, for example, in embodiments employing an M13 selection phage, the host cells are *E. coli* cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of *E. coli* cells with certain phage, for example, with M13 phage. For example, in some embodiments, the host cells for M13-PACE are of the genotype F'proA$^+$B$^+$Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ$^-$.

The general concept of PACE technology has been described, for example in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. Application, U.S. Ser. No. 13/922,812, filed Jun. 20, 2013, each of which is incorporated herein by reference.

Methods for Evolving Recombinases

Some aspects of this disclosure provide methods for evolving recombinases. In some embodiments, the methods comprise (a) contacting a population of host cells with a population of phage vectors comprising a gene encoding a recombinase and deficient in at least one gene for the generation of infectious phage particles, wherein (1) the host cells are amenable to transfer of the phage vector; (2) the vector allows for expression of the recombinase in a host cell, can be replicated by the host cell, and the replicated vector can transfer from host cell to host cell; (3) the host cells express a gene product encoded by the at least one gene for the generation of infectious phage particles of (a) in response to the recombination of a recombinase target sequence by the recombinase, and the level of gene product expression depends on the activity of the recombinase towards the target sequence; (b) incubating the population of host cells under conditions allowing for mutation of the gene encoding the recombinase and the transfer of the phage vectors from host cell to host cell, wherein host cells are removed from the host cell population, and the population of host cells is replenished with fresh host cells that do not harbor the phage vector; and (c) isolating a replicated phage vector from the host cell population in (b), wherein the replicated vector comprises a mutated version of the gene encoding the recombinase.

In some embodiments, the host cells harbor an expression construct comprising a nucleotide sequence encoding a gene product of the at least one gene for the generation of infectious phage particles of (a) under the control of a heterologous promoter and a transcriptional terminator flanked by two recombinase target sequences. In some embodiments, the recombinase target sequences are different from the target sequences recognized by the wild-type version of the recombinase. In some embodiments, recombination of the recombinase target sequences results in excision of the transcriptional terminator and expression of the at least one gene for the generation of infectious phage particles. In some embodiments, the recombinase is a Cre recombinase. In some embodiments, the replicated vector isolated in (c) encodes a mutated recombinase that cleaves the recombinase target sequence with higher efficiency than the version of the recombinase of (a). In some embodiments, the recombinase target sequence comprises a sequence occurring in the genome of a target cell. In some embodiments, the recombinase target sequence comprises a sequence occurring once in the genome of a target cell. In some embodiments, the recombinase target sequence comprises a sequence occurring in a ubiquitously expressed genomic locus. In some embodiments, the recombinase target sequence comprises a sequence occurring in the Rosa 26 locus of the target cell. In some embodiments, the recombinase target sequence comprises a mammalian genomic sequence. In some embodiments, the recombinase target sequence comprises a human genomic sequence. In some embodiments, the recombinase target sequence comprises a sequence within a mammalian genome and wherein the recombinase target sequence differs from any other sequence of the same length within the genome in at least 1, at least 2, at least 3, at least 4, at least 5, at least 6, at least 7, at least 8, at least 9, or at least 10 nucleotides. In some embodiments, the vector is a viral vector. In some embodiments, the viral vector is a phage. In some embodiments, the phage is a filamentous phage. In some embodiments, the phage is an M13 phage. In some embodiments, the at least one gene for the generation of infectious phage particles comprises a sequence encoding a pIII protein. In some embodiments, the at least one gene for the generation of infectious phage particles comprises a full-length gIII gene. In some embodiments, the host cells comprise all phage genes except for the at least one gene for the generation of infectious phage particles in the form of a helper phage. In some embodiments, the phage genes comprised on the helper phage comprise pI, pII, pIV, pV, pVI, pVII, pVIII, pIX, and/or pX. In some embodiments, one, some, or all phage genes except for the at least one gene for the generation of infectious phage particles are provided to the host cell by the phage vector of (a) or a mutated progeny vector of the phage vector of (a). In some embodiments, the host cells comprise an accessory plasmid and together, the phage vector of (a) and the accessory plasmid comprise all genes required for the generation of an infectious phage. In some embodiments, the host cells comprise an accessory plasmid, and wherein the accessory plasmid comprises an expression construct encoding the pIII protein under the control of a heterologous promoter and a transcriptional terminator flanked by two recombinase target sequences.

In some embodiments, the method further comprises a negative selection for undesired recombinase activity. In some embodiments, the host cells comprise an expression construct encoding a dominant-negative pIII protein (pIII-neg), and wherein the expression of the pIII-neg protein depends on the undesired recombinase activity. In some embodiments, expression of the pIII-neg protein is activated by recombination of undesired recombinase target sequences flanking a transcriptional terminator within the expression construct encoding the pIII-neg protein. In some embodiments, the undesired recombinase target sequences are off-target recombinase target sequences. In some embodiments, the undesired recombinase target sequences are sequences recognized by the wild-type version of the recombinase of (a).

In some embodiments, the host cells further comprise a mutagenesis plasmid.

In some embodiments, the host cells are E. coli cells. In some embodiments, the host cells are incubated in suspension culture. In some embodiments, the population of host cells is continuously replenished with fresh host cells that do not comprise the phage vector. In some embodiments, fresh cells are being replenished and cells are being removed from the cell population at a rate resulting in a substantially constant number of cells in the cell population. In some embodiments, fresh cells are being replenished and cells are being removed from the cell population at a rate resulting in a substantially constant phage vector population.

In some embodiments, the method comprises a phase of diversifying the population of phage vectors by mutagenesis, in which the cells are incubated under conditions suitable for mutagenesis of the gene encoding the recombinase in the absence of stringent selection for vectors having acquired a mutation in the gene encoding the recombinase. In some embodiments, the method comprises a phase of stringent selection for a mutated replication product of the phage vector encoding an evolved recombinase.

Some aspects of this disclosure provide evolved recombinases obtained by the phage-assisted continuous evolution methods provided herein.

Evolved Recombinases

Some aspects of this disclosure provide evolved recombinases comprising an amino acid sequence that is at least 70%, at least 80%, at least 90%, at least 95%, or at least 97% identical to the sequence of a wild-type recombinase, wherein the amino acid sequence of the evolved recombinase comprises at least one mutation as compared to the sequence of the wild-type recombinase, and wherein the evolved recombinase recognizes a DNA recombinase target sequence that differs from the canonical recombinase target sequence by at least one nucleotide. In some embodiments, In some embodiments, the evolved recombinase recognizes a DNA recombinase target sequence that differs from the canonical recombinase target sequence by at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 at least 25, or at least 30 nucleotides. In some embodiments, the evolved recombinase recognizes a DNA recombinase target sequence that differs from the canonical recombinase target sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, the recombinase target sequence is between 10-50 nucleotides long. In some embodiments, the recombinase is a Cre recombinase, a Hin recombinase, or a FLP recombinase. In some embodiments, the canonical recombinase target sequence is a LoxP site (5'-ATAACTTCGTATA GCATACAT TATACGAAGTTAT-3', SEQ ID NO: 2). In some embodiments, the canonical recombinase target sequence is an FRT site (5'-5'-GAAGTTCCTATTCTCTAGAAA GTATAGGAACTTC-3', SEQ ID NO: 3). In some embodiments, the amino acid sequence of the recombinase comprises at least 2, at least 3, at least 4, at least 5, at least 6, at least 7, at least 8, at least 9, at least 10, at least 11, at least 12, at least 13, at least 14, or at least 15 mutations as compared to the sequence of the wild-type recombinase. In some embodiments, the recombinase recognizes a DNA recombinase target sequence that comprises a left half-site, a spacer sequence, and a right half-site, and wherein the left half-site is not a palindrome of the right half-site.

In some embodiments, the recombinase recognizes a DNA recombinase target sequence that comprises a naturally occurring sequence. In some embodiments, the recombinase recognizes a DNA recombinase target sequence that is comprised in the genome of a mammal. In some embodiments, the recombinase recognizes a DNA recombinase target sequence comprised in the genome of a human. In some embodiments, the recombinase recognizes a DNA recombinase target sequence that occurs only once in the genome of a mammal. In some embodiments, the recombinase recognizes a DNA recombinase target sequence in the genome of a mammal that differs from any other site in the genome by at least 1, at least 2, at least 3, at least 4, at least 5, at least 6, at least 7, at least 8, at least 9, at least 10, at least 11, at least 12, at least 13, at least 14, or at least 15 nucleotide(s). In some embodiments, the recombinase recognizes a DNA recombinase target sequence located in a safe harbor genomic locus. In some embodiments, the safe harbor genomic locus is a Rosa26 locus. In some embodiments, the recombinase recognizes a DNA recombinase target sequence located in a genomic locus associated with a disease or disorder.

Some aspects of this disclosure provide pharmaceutical compositions comprising a recombinase as provided herein and a pharmaceutically acceptable excipient. In some embodiments, the pharmaceutical composition is formulated for administration to a subject. In some embodiments, the pharmaceutical composition comprises an effective amount of the recombinase for recombining a recombinase target sequence in a cell of a subject in vivo, ex vivo, or in vitro. In some embodiments, the composition further comprises a nucleic acid molecule comprising at least one recombinase target sequence adjacent to a sequence to be inserted into a genetic locus within the genome of the subject. In some embodiments, the nucleic acid molecule is a circular DNA molecule comprising a single recombinase target sequence.

Some aspects of this disclosure provide Cre recombinases comprising an amino acid sequence that is at least 70%, at least 80%, at least 90%, at least 95%, or at least 97% identical to the sequence of SEQ ID NO: 1, wherein the amino acid sequence of the Cre recombinase comprises at least one mutation as compared to the sequence of SEQ ID NO: 1, and wherein the Cre recombinase recognizes a DNA recombinase target sequence that differs from the canonical LoxP site 5'-ATAACTTCGTATA GCATACAT TATACGAAGTTAT-3' (SEQ ID NO: 2) in at least one nucleotide.

In some embodiments, the amino acid sequence of the Cre recombinase comprises at least 2, at least 3, at least 4, at least 5, at least 6, at least 7, at least 8, at least 9, at least 10, at least 11, at least 12, at least 13, at least 14, or at least 15 mutations as compared to the sequence of SEQ ID NO: 1. In some embodiments, the Cre recombinase recognizes a DNA recombinase target sequence that differs from the canonical LoxP site in at least 1, at least 2, at least 3, at least 4, at least 5, at least 6, at least 7, at least 8, at least 9, at least 10, at least 11, at least 12, at least 13, at least 14, or at least 15 nucleotides.

In some embodiments, the Cre recombinase recognizes a DNA recombinase target sequence that comprises a left half-site, a spacer sequence, and a right half-site, wherein the left half-site is not a palindrome of the right half-site. In some embodiments, the Cre recombinase recognizes a DNA recombinase target sequence that comprises a naturally occurring sequence. In some embodiments, the Cre recombinase recognizes a DNA recombinase target sequence that is comprised in the genome of a mammal.

In some embodiments, the Cre recombinase recognizes a DNA recombinase target sequence that is comprised in the genome of a human. In some embodiments, the Cre recombinase recognizes a DNA recombinase target sequence that is comprised only once in the genome of a mammal. In some embodiments, the Cre recombinase recognizes a DNA recombinase target sequence in the genome of a mammal that differs from any other site in the genome by at least 1, at least 2, at least 3, at least 4, at least 5, at least 6, at least 7, at least 8, at least 9, at least 10, at least 11, at least 12, at least 13, at least 14, or at least 15 nucleotide(s).

In some embodiments, the Cre recombinase recognizes a DNA recombinase target sequence located in a safe harbor genomic locus. In some embodiments, the safe harbor genomic locus is a Rosa26 locus.

In some embodiments, the Cre recombinase recognizes a DNA recombinase target sequence located in a genomic locus associated with a disease or disorder.

Some aspects of this disclosure provide pharmaceutical compositions comprising a Cre recombinase as provided herein and a pharmaceutically acceptable excipient In some embodiments, the pharmaceutical composition is formulated for administration to a subject. In some embodiments, the pharmaceutical composition comprises an effective amount of the Cre recombinase for recombining a recombinase target sequence in a cell in the subject. In some embodiments, the composition further comprises a nucleic acid molecule comprising at least one recombinase target sequence adjacent to a sequence to be inserted into a genetic locus within the genome of the subject. In some embodiments, the nucleic acid molecule is a circular DNA molecule comprising a single recombinase target sequence.

Methods For Recombinase-Mediated Genetic Engineering

Some aspects of this disclosure provide methods for engineering a nucleic acid molecule, the method comprising contacting a first nucleic acid molecule comprising a first recombinase target sequence of the structure 5'-[left half-site]-[spacer]-[right half-site]-3' with a recombinase and a second nucleic acid molecule comprising a second recombinase target sequence under conditions suitable for the recombinase to bind and recombine the recombinase target sequences, wherein the first and the second recombinase target sequences differ from the canonical Cre recombinase target sequence 5'-ATAACTTCGTATA GCATACAT TATACGAAGTTAT-3' (SEQ ID NO: 2) in at least 1, at least 2, at least 3, at least 4, at least 5, at least 6, at least 7, at least 8, at least 9, at least 10, at least 11, at least 12, at least 13, at least 14, or at least 15 nucleotides.

In some embodiments, the left half-site of the recombinase target sequence is not a palindrome of the right half-site. In some embodiments, the recombinase target sequence comprises a naturally occurring sequence. In some embodiments, the recombinase target sequence is comprised in the genome of a mammal. In some embodiments, the recombinase target sequence is comprised in the genome of a human. In some embodiments, the recombinase target site is comprised only once in the genome of a mammal.

In some embodiments, the recombinase target sequence is comprised in the genome of a mammal and differs from any other site in the genome by at least 1, at least 2, at least 3, at least 4, at least 5, at least 6, at least 7, at least 8, at least 9, at least 10, at least 11, at least 12, at least 13, at least 14, or at least 15 nucleotide(s).

In some embodiments, the recombinase target sequence is located in a safe harbor genomic locus. In some embodiments, the safe harbor genomic locus is a Rosa26 locus. In some embodiments, the recombinase target sequence is located in a genomic locus associated with a disease or disorder.

In some embodiments, the first nucleic acid molecule is contacted with the recombinase in a cell. In some embodiments, the contacting is in vitro. In some embodiments, the contacting is in vivo. In some embodiments, the method comprises administering A composition comprising the recombinase and the second nucleic acid molecule to the subject in an amount sufficient for the recombinase to bind and recombine the first recombinase target sequence.

In some embodiments, a method is provided that comprises contacting the genome of a cell with an evolved recombinase provided herein, either in vivo, ex vivo, or in vitro, wherein the contacting results in the evolved recombinase binding and recombining a recombinase target sequence within the genome of the cell, thus altering the sequence of the genome. In some embodiments, the change in the genome comprises an excision of a sequence associated with a disease or disorder, such as, for example, a mutated version of a gene, or an integrated viral genome. In some embodiments, the contacting results in the integration of a heterologous nucleic acid sequence into the genome of the cell, e.g., at a safe harbor locus or in place of an undesired sequence.

Methods for Evaluating the Specificity of Recombinases

Some aspects of this disclosure provide methods for identifying a target site of a recombinase. In some embodiments, the comprises (a) providing a recombinase that binds and recombines a double-stranded nucleic acid target sequence of the structure 5'-[left half-site]-[spacer]-[right half-site]-3; (b) contacting the recombinase of (a) with a library of candidate nucleic acid molecules, wherein each candidate nucleic acid molecule comprises a nucleic acid strand comprising the structure 5'-[spacer]-[half-site]-[loop sequence]-[half-site]-[spacer]-3', wherein the spacer and half-site sequences on the 5' and 3' end are complementary and hybridize to each other, thus forming a single-stranded loop structure and a double-stranded [half-site]-[spacer] structure, and wherein each candidate nucleic acid molecule comprises a PCR primer binding site within the loop sequence, under conditions suitable for the recombinase to bind a candidate nucleic acid molecule comprising a [spacer]-[half-site]-structure and recombine it with the [spacer]-[half-site] structure of a different candidate nucleic acid molecule, thus creating a recombed circular nucleic acid molecule comprising a [loop sequence]-[half-site]-[spacer]-[half-site]-[loop sequence] structure; and (c) identifying recombinase target sites bound and recombined by the recombinase in (b) by determining the sequence of the [half-site]-[spacer]-[half-site] structure of the recombined circular nucleic acid molecule in (b).

In some embodiments, the determining of step (c) comprises amplifying a fragment comprising the [half-site]-[spacer]-[half-site] of the recombined nucleic acid molecule via a PCR reaction using a PCR primer that hybridizes with the primer binding site within the loop sequence. In some embodiments, the method further comprises enriching the amplified nucleic acid molecules for molecules comprising a [half-site]-[spacer]-[half-site] structure. In some embodiments, the enriching comprises a size fractionation. In some embodiments, the determining of step (c) comprises sequencing the [half-site]-[spacer]-[half-site] structure of a nucleic acid molecule that was recombined by the recombinase in step (b), or a copy thereof obtained via PCR. In some embodiments, the method further comprises contacting the library of candidate molecules with an exonuclease after completion of step (b). In some embodiments, the library of candidate nucleic acid molecules comprises at least $10^8$, at least $10^9$, at least $10^{10}$, at least $10^{11}$, or at least $10^{12}$ different half-site sequences.

In some embodiments, the loop sequence and/or the spacer sequence is identical amongst the candidate nucleic acid molecules of the library. In some embodiments, the recombinase binds and recombines a specific recombinase target sequence within a genome. In some embodiments, the left half-site of the recombinase target sequence is not a palindrome of the right half-site. In some embodiments, the recombinase target sequence comprises a naturally occurring sequence.

In some embodiments, the library comprises at least one copy of each possible half-site sequence occurring within a genome. In some embodiments, the library comprises at least two-fold, at least four-fold, at least five-fold, or at least ten-fold coverage of each possible half-site sequence occurring within a genome.

In some embodiments, the method further comprises determining a maximum concentration of the recombinase at which the recombinase binds and recombines a specific recombinase target sequence, and does not recombine more than 10, more than 5, more than 4, more than 3, more than 2, more than 1, or no additional recombinase target sequences. In some embodiments, the method further comprises determining all recombinase target sequences bound and recombined by the recombinase.

In some embodiments, the method further comprises generating a recombinase target sequence profile for the recombinase.

In some embodiments, the method comprises subjecting a plurality of recombinases that bind and recombine a consensus target sequence to steps (a)-(c), thus identifying any off-target sequences bound and recombined by each of the recombinases, and selecting a recombinase based on the off-target site(s) so identified. In some embodiments, the recombinase selected is the recombinase that binds and recombines the consensus target sequence with the highest specificity.

In some embodiments, the recombinase that binds and recombines the consensus target sequence with the highest specificity is the recombinase that binds and recombines the lowest number of off-target sequences. In some embodiments, the recombinase that binds and recombines the consensus target sequence with the highest specificity is the recombinase that binds and recombines the lowest number of off-target sequences that are different from the consensus site in the context of a target genome. In some embodiments, the recombinase selected is the recombinase that binds and recombines no sequence other than the consensus target sequence.

In some embodiments, the recombinase selected is the recombinase that binds and recombines the consensus target sequence but no sequence other than the consensus target sequence when contacted with all possible target sequences that occur within the genome of a subject.

Libraries for Assessing Recombinase Target Site Preferences

Some aspects of this disclosure provide libraries of nucleic acid molecules that are useful for assessing the target sites preferences of recombinases. In some embodiments the library comprises a plurality of nucleic acid molecules, wherein each nucleic acid molecule comprises a 5'-[spacer]-[half-site]-[loop sequence]-[half-site]-[spacer]-3' structure, wherein the spacer and half-site sequences on the 5' and 3' end are complementary and hybridize to each other, thus forming a single-stranded loop structure and a double-stranded [half-site]-[spacer] structure, and wherein each candidate nucleic acid molecule comprises a PCR primer binding site within the loop sequence.

In some embodiments, the loop sequence is at least 15, at least 20, at least 25, at least 30, at least 35, at least 40, at least 45, at least 50, at least 55, at least 60, at least 65, at least 70, at least 75, at least 80, at least 90, at least 95, at least 100, at least 150, at least 200, at least 250, at least 300, at least 350, at least 400, at least 450, at least 500, at least 550, at least 600, at least 650, at least 700, at least 750, at least 800, at least 900, at least 950, or at least 1000 nucleotides long.

In some embodiments, the loop sequence is not more than 15, not more than 20, not more than 25, not more than 30, not more than 35, not more than 40, not more than 45, not more than 50, not more than 55, not more than 60, not more than 65, not more than 70, not more than 75, not more than 80, not more than 90, not more than 95, not more than 100, not more than 150, not more than 200, not more than 250, not more than 300, not more than 350, not more than 400, not more than 450, not more than 500, not more than 550, not more than 600, not more than 650, not more than 700, not more than 750, not more than 800, not more than 900, not more than 950, or not more than 1000 nucleotides long.

In some embodiments, the library comprises at least $10^5$, at least $10^6$, at least $10^7$, at least $10^8$, at least $10^9$, at least $10^{10}$, at least $10^{11}$, or at least $10^{12}$ different candidate half-site sequences.

In some embodiments, the loop sequence and/or the spacer sequence is identical amongst nucleic acid molecules comprising different half-site sequences. In some embodiments, the library comprises candidate recombinase target half-sites that are variations of a known target half-site of a recombinase of interest. In some embodiments, the variations of the known recombinase target half-site comprise 10 or fewer, 9 or fewer, 8 or fewer, 7 or fewer, 6 or fewer, 5 or fewer, 4 or fewer, 3 or fewer, or 2 or fewer mutations as compared to the known recombinase target half-site.

Vectors and Reagents

Some aspects of this disclosure provide vectors and reagents for carrying out the inventive continuous recombinase evolution processes.

In some embodiments, a selection phage is provided that comprises a phage genome deficient in at least one gene required for the generation of infectious phage particles and a gene encoding a recombinase of interest to be evolved.

For example, in some embodiments, a selection phage as described in in PCT Application PCT/US2009/056194, published as WO2010/028347 on Mar. 11, 2010; PCT Application PCT/US2011/066747, published as WO2012/088381 on Jun. 28, 2012; and U.S. Nonprovisional application Ser. No. 13/922,812, filed on Jun. 20, 2013, the entire contents of each of which are incorporated herein by reference, is provided, that comprises a multiple cloning site for insertion of a nucleic acid sequence encoding a recombinase of interest.

Such selection phage vectors typically comprise an M13 phage genome deficient in a gene required for the generation of infectious M13 phage particles, for example, a full-length gIII. In some embodiments, the selection phage comprises a phage genome providing all other phage functions required for the phage life cycle except the gene required for generation of infectious phage particles. In some such embodiments, an M13 selection phage is provided that comprises a gI, gII, gIV, gV, gVI, gVII, gVIII, gIX, and a gX gene, but not a full-length gIII. In some embodiments, the selection phage comprises a 3'-fragment of gIII, but no full-length gIII. The 3'-end of gIII comprises a promoter and retaining this promoter activity is beneficial, in some embodiments, for an increased expression of gVI, which is immediately downstream of the gIII 3'-promoter, or a more balanced (wild-type phage-like) ratio of expression levels of the phage genes in the host cell, which, in turn, can lead to more efficient phage production. In some embodiments, the 3'-fragment of gIII gene comprises the 3'-gIII promoter sequence. In some embodiments, the 3'-fragment of gIII comprises the last 180 bp, the last 150 bp, the last 125 bp, the last 100 bp, the last 50 bp, or the last 25 bp of gIII. In some embodiments, the 3'-fragment of gIII comprises the last 180 bp of gIII. In some embodiments, the multiple cloning site for insertion of the gene encoding the recombinase of interest is located downstream of the gVIII 3'-terminator and upstream of the gIII-3'-promoter.

In some embodiments, the selection phage is an M13 phage as described herein. For example, in some embodiments, the selection phage comprises an M13 genome including all genes required for the generation of phage particles, for example, gI, gII, gIV, gV, gVI, gVII, gVIII, gIX, and gX gene, but not a full-length gIII gene. In some embodiments, the selection phage genome comprises an F1 or an M13 origin of replication. In some embodiments, the selection phage genome comprises a 3'-fragment of gIII gene. In some embodiments, the selection phage comprises a multiple cloning site upstream of the gIII 3'-promoter and downstream of the gVIII 3'-terminator for insertion of a gene encoding a recombinase of interest.

The vector system may further comprise a helper phage, wherein the selection phage does not comprise all genes for the generation of infectious phage particles, and wherein the helper phage complements the genome of the selection phage, so that the helper phage genome and the selection phage genome together comprise at least one functional copy of all genes for the generation of phage particles, but are deficient in at least one gene required for the generation of infectious phage particles, which is provided by an accessory plasmid.

In some embodiments, the vector system further comprises a mutagenesis plasmid, for example, an arabinose-inducible mutagenesis plasmid as described herein. In some embodiments, the mutagenesis plasmid comprises a gene expression cassette encoding a component of *E. coli* translesion synthesis polymerase V, a deoxyadenosine methylase, and/or a hemimethylated-GATC binding domain, or any combination thereof. In some embodiments, the component of *E. coli* translesion synthesis polymerase V is umuC. In some embodiments, the deoxyadenosine methylase is dam. In some embodiments, the hemimethylated-GATC binding domain is seqA.

Expression Constructs

Some aspects of this disclosure provide nucleic acids encoding any of the recombinases provided herein. In some embodiments, the nucleic acids encoding the recombinases are under the control of a heterologous promoter. In some embodiments, the encoding nucleic acids are included in an expression construct, e.g., a plasmid, a viral vector, or a linear expression construct. In some embodiments, the nucleic acid or expression construct is in a cell, tissue, or organism.

Nucleic acids encoding any of the proteins, described herein, may be in any number of nucleic acid "vectors" known in the art. As used herein, a "vector" means any nucleic acid or nucleic acid-bearing particle, cell, or organism capable of being used to transfer a nucleic acid into a host cell. The term "vector" includes both viral and nonviral products and means for introducing the nucleic acid into a cell. A "vector" can be used in vitro, ex vivo, or in vivo. Non-viral vectors include plasmids, cosmids, artificial chromosomes (e.g., bacterial artificial chromosomes or yeast artificial chromosomes) and can comprise liposomes, electrically charged lipids (cytofectins), DNA-protein complexes, and biopolymers, for example. Viral vectors include retroviruses, lentiviruses, adeno-associated virus, pox viruses, baculovirus, reoviruses, vaccinia viruses, herpes simplex viruses, Epstein-Barr viruses, and adenovirus vectors, for example. Vectors can also comprise the entire genome sequence or recombinant genome sequence of a virus. A vector can also comprise a portion of the genome that comprises the functional sequences for production of a virus capable of infecting, entering, or being introduced to a cell to deliver nucleic acid therein.

Expression of any of the recombinases described herein may be controlled by any regulatory sequence (e.g. a promoter sequence) known in the art. Regulatory sequences, as described herein, are nucleic acid sequences that regulate the expression of a nucleic acid sequence. A regulatory or control sequence may include sequences that are responsible for expressing a particular nucleic acid (e.g., a nucleic acid encoding a recombinases) or may include other sequences, such as heterologous, synthetic, or partially synthetic sequences. The sequences can be of eukaryotic, prokaryotic or viral origin that stimulate or repress transcription of a gene in a specific or non-specific manner and in an inducible or non-inducible manner. Regulatory or control regions may include origins of replication, RNA splice sites, introns, chimeric or hybrid introns, promoters, enhancers, transcriptional termination sequences, poly A sites, locus control regions, signal sequences that direct the polypeptide into the secretory pathways of the target cell, and introns. A heterologous regulatory region is not naturally associated with the expressed nucleic acid it is linked to. Included among the heterologous regulatory regions are regulatory regions from a different species, regulatory regions from a different gene, hybrid regulatory sequences, and regulatory sequences that do not occur in nature, but which are designed by one of ordinary skill in the art.

The term operably linked refers to an arrangement of sequences or regions wherein the components are configured so as to perform their usual or intended function. Thus, a regulatory or control sequence operably linked to a coding sequence is capable of affecting the expression of the coding sequence. The regulatory or control sequences need not be contiguous with the coding sequence, so long as they function to direct the proper expression or polypeptide production. Thus, for example, intervening untranslated but transcribed sequences can be present between a promoter sequence and the coding sequence and the promoter sequence can still be considered operably linked to the coding sequence. A promoter sequence, as described herein, is a DNA regulatory region a short distance from the 5' end of a gene that acts as the binding site for RNA polymerase. The promoter sequence may bind RNA polymerase in a cell and/or initiate transcription of a downstream (3' direction) coding sequence. The promoter sequence may be a promoter capable of initiating transcription in prokaryotes or eukaryotes. Some non-limiting examples of eukaryotic promoters include the cytomegalovirus (CMV) promoter, the chicken β-actin (CBA) promoter, and a hybrid form of the CBA promoter (CBh).

Some aspects of this disclosure provide cells expressing an evolved recombinase provided herein, e.g., by virtue of harboring an expression construct as described above. In some embodiments, cells contacted with a recombinase as provided herein are provided, e.g., cells contacted in vitro, in vivo, or ex vivo.

Host Cells

Some aspects of this invention relate to host cells for continuous evolution processes as described herein. In some embodiments provide host cells for phage-assisted continuous evolution processes, wherein the host cell comprises an accessory plasmid comprising a gene required for the generation of infectious phage particles, for example, M13 gIII, that is expressed only in the presence of a desired recombinase activity, as described herein. In some embodiments, the host cell further provides any phage functions that are not contained in the selection phage, e.g., in the form of a helper phage. In some embodiments, the host cell provided further comprises an expression construct comprising a gene encoding a mutagenesis-inducing protein, for example, a mutagenesis plasmid as provided herein.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of infectious viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a recombinase of interest able to activate expression of the gene, but it is still a suitable host cell for such a viral vector.

In some embodiments, the host cell is a prokaryotic cell, for example, a bacterial cell. In some embodiments, the host cell is an $E.\ coli$ cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some embodiments, the viral vector is a phage and the host cell is a bacterial cell. In some embodiments, the host cell is an $E.\ coli$ cell. Suitable $E.\ coli$ host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect.

In some PACE embodiments, for example, in embodiments employing an M13 selection phage, the host cells are $E.\ coli$ cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of $E.\ coli$ cells with certain phage, for example, with M13 phage. For example, in some embodiments, the host cells for M13-PACE are of the genotype F'proA$^+$B$^+$Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ⁻.

Kits and Apparatuses

Some aspects of this invention provide kits for continuous recombinase evolution as described herein. In some embodiments, the kit comprises (a) a vector encoding a phage backbone, for example, an M13 phage backbone, and a multiple cloning site for insertion of a nucleic acid sequence encoding a recombinase. In some embodiments, the vector or a replication product thereof can be packaged into infectious phage particles in the presence of other phage functions by suitable host cells. In some embodiments, the vector or a replication product thereof lacks at least one gene required for the generation of infectious particles.

In some embodiments, the kit comprises (b) an accessory plasmid comprising a nucleic acid sequence encoding the at least one gene required for the generation of infectious particles and a recombinase target site, wherein recombination of the recombinase target site by the recombinase to be evolved is required to activate expression of the at least one gene.

In some embodiments, the kit further comprises a helper phage providing all phage functions except for the at least one gene required for the generation of infectious phage particles provided by the accessory plasmid of (b). In some embodiments, the helper phage or a replication product thereof cannot be packaged into infectious phage particles.

In some embodiments, the kit comprises suitable host cells. In some embodiments, the host cells are $E.$ $coli$ host cells. In some embodiments, the kit further comprises a mutagenesis plasmid. In some embodiments, the mutagenesis plasmid comprising a gene expression cassette encoding umuC (a components of $E.$ $coli$ translesion synthesis polymerase V), dam (deoxyadenosine methylase), and/or seqA (a hemimethylated-GATC binding domain), or any combination thereof.

In some embodiments, a PACE apparatus is provided, comprising a lagoon that is connected to a turbidostat comprising a host cell as described herein. In some embodiments, the host cell is an $E.$ $coli$ host cell. In some embodiments, the host cell comprises an accessory plasmid as described herein, a helper plasmid as described herein, and/or a mutagenesis plasmid as described herein. In some embodiments, the lagoon further comprises a selection phage as described herein, for example, a selection phage encoding a recombinase of interest. In some embodiments, the lagoon is connected to a vessel comprising an inducer for a mutagenesis plasmid, for example, arabinose. In some embodiments, the host cells are $E.$ $coli$ cells comprising the F' plasmid, for example, cells of the genotype F'proA⁺B⁺Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ⁻.

For example, in some embodiments, a PACE apparatus is provided, comprising a lagoon of about 100 ml, or about 1 l volume, wherein the lagoon is connected to a turbidostat of about 0.5 l, 1 l, or 3 l volume, and to a vessel comprising an inducer for a mutagenesis plasmid, for example, arabinose, wherein the lagoon and the turbidostat comprise a suspension culture of $E.$ $coli$ cells at a concentration of about 5×10⁸ cells/ml. In some embodiments, the flow of cells through the lagoon is regulated to about 3 lagoon volumes per hour. In some embodiments, cells are removed from the lagoon by continuous pumping, for example, by using a waste needle set at a height of the lagoon vessel that corresponds to a desired volume of fluid (e.g., about 100 ml, in the lagoon. In some embodiments, the host cells are $E.$ $coli$ cells comprising the F' plasmid, for example, cells of the genotype F'proA⁺B⁺Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ⁺.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

A Phage Assisted Continuous Evolution (PACE) selection for rapidly altering the DNA specificity of Cre recombinase towards a site present in a human genomic safe harbor locus, Rosa 26, was developed. The PACE experiments resulted in Cre variants capable of recombining a substrate with nearly 50% of the nucleotides altered compared to LoxP. We successfully used one of these variants to integrate exogenous DNA into the genome of unmodified human cells.

Figure 2:
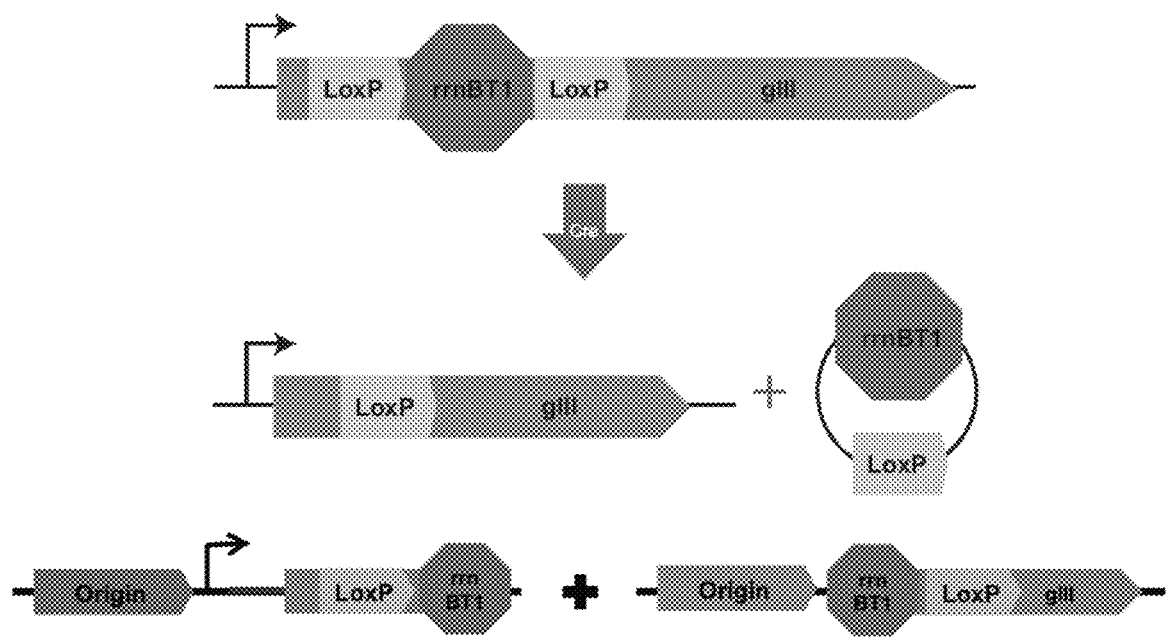
FIG. 2. Schematic illustration of an exemplary embodiment of a Cre-deletion-dependent Accessory Plasmid (AP) (upper panel), and of a Cre-integration-dependent Accessory Plasmid (lower panel).

A Cre deletion-dependent Accessory Plasmid (AP) was generated (FIG. 2). Expression of the essential phage gene III (gIII) encoding the envelope protein III (pIII) is prevented by the strong transcriptional terminator rrnBT1, which is flanked by two Cre recombinase target sequences (LoxP sites). To lower background expression, the deletion cassette was placed internal to the gIII-encoding sequence. Recombination by Cre results in a deletion of the rrnBT1 terminator and thus to expression of gIII. Cells harboring the native AP do not express a functional gIII, and thus do not support the production of infectious phage particles. Upon Cre-mediated recombination, resulting in the deletion of the terminator, a functional gIII is reconstituted, thus enabling phage propagation.

In order to enable the evolution of recombinases based on the integration of two nucleic acid constructs comprising altered LoxP sites, a selection system was developed that comprises two cassettes, which, in their original state, do not confer expression of gIII to the host cells, but require integration via recombinase activity to reconstitute a functional expression construct encoding gIII (FIG. 2, lower panel). This selection strategy is useful for selecting recombinase activity based on the integration of two nucleic acid cassettes. The schematic in the lower panel of FIG. 2 shows two exemplary cassettes. Integration of these two constructs reconstitutes an intact gIII—identical to the gene product resulting from recombining the plasmid in the upper panel of FIG. 2. The selection stringency can be tuned by choosing high or low copy origins for either plasmids, as well as altering the promoter or ribosomal binding site strength on the upstream plasmid.

Figure 3:
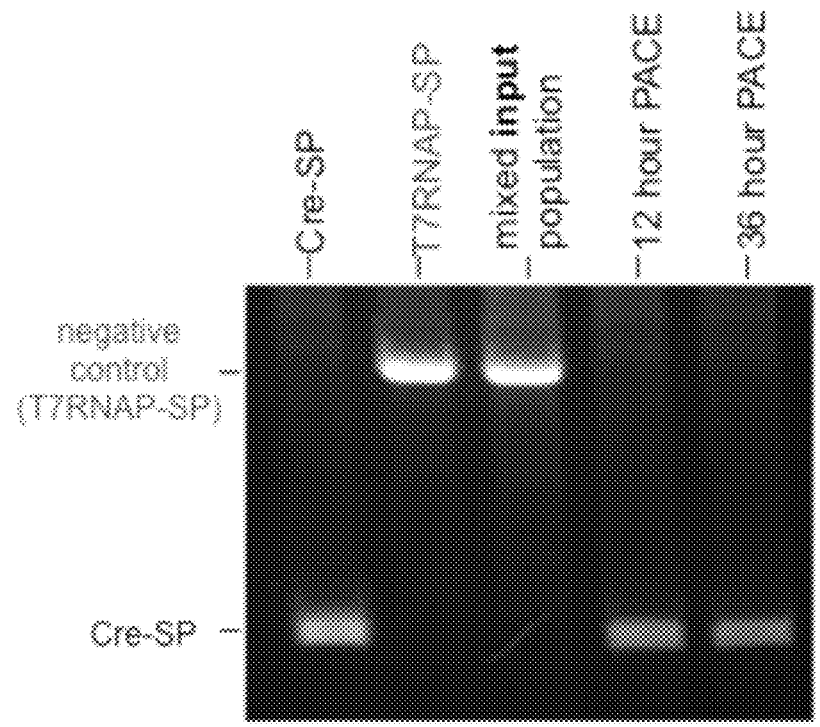
FIG. 3. Selection Validation. PACE selection was observed to enrich Cre-SP from a 1:1×10$^6$ SP mixture within 12 hrs.

In order to validate the selection strategy, a PACE experiment was performed with host cells harboring a recombinase-deletion-dependent AP as outlined in the upper panel of FIG. 2 with native LoxP sites and a selection phagemid encoding Cre (positive control). FIG. 3 shows that the Cre-selection phagemid propagated within the host cell population and could be retrieved from the lagoon. A second PACE experiment was performed with a selection phagemid encoding T7 RNA polymerase (negative control). The T7RNAP selection phagemid did not propagate and could not be retrieved from the lagoon. In order to test whether the PACE setup with the Cre deletion-dependent AP was able to enrich selection phagemid encoding a recombinase having the desired activity from a pool of phagemids with an excess of inactive members, a mixture of (active) Cre-encoding selection phagemid and (inactive) T7RNAP phagemid at a ratio of $1:1\times10^6$ was used in a third PACE experiment. As shown in FIG. 3, the PACE set up was able to enrich for Cre-SP within 12 hours.

Figure 4:
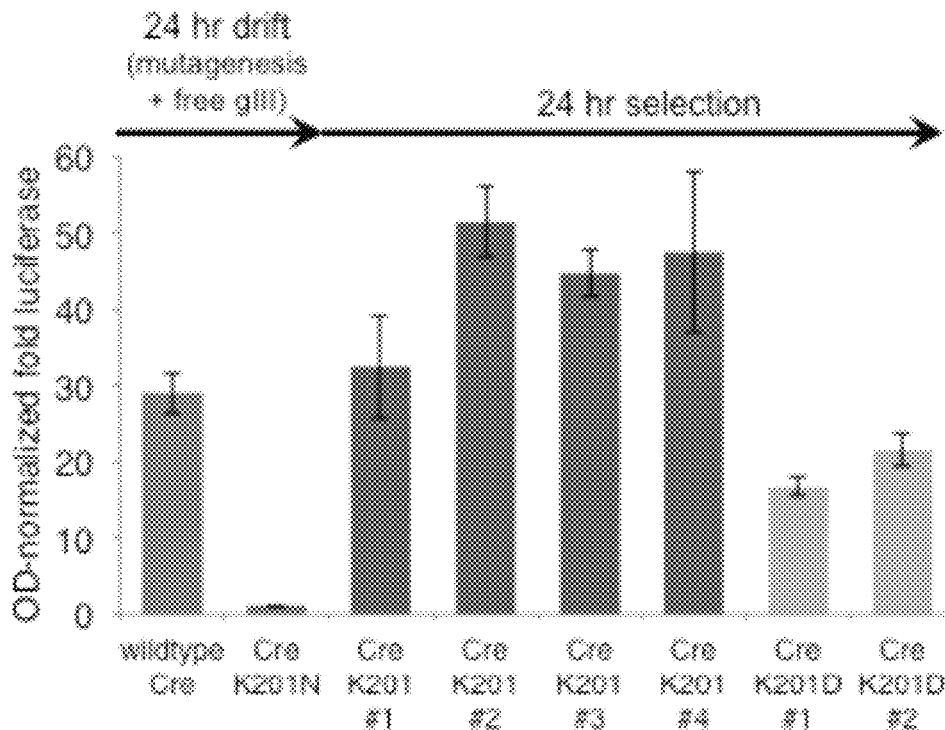
FIG. 4. Selection Validation. Drift and selection were observed to be capable of isolating multiple active mutants from a catalytically inactive (K201N) starting point.

In order to test whether inactive Cre proteins could be evolved to recognize the native LoxP site, a PACE experiment starting with the catalytically inactive K201N Cre mutant was carried out. The experiment included an initial 24 hr period in which the host cells were incubated under mutagenic conditions and gIII was provided from an inducible promoter and thus the selective pressure for functional Cre was removed. This initial period allowed mutagenesis and drift of the phagemid population. After the initial 24 hour period, selective pressure for functional Cre molecules was imposed by removing expression of gIII from the inducible promoter, so that any gIII expression had to be driven off the Cre deletion-dependent AP. FIG. 4 demonstrates that drift and selection can isolate multiple active Cre mutants from a catalytically inactive starting point. The recombinase activity of evolved Cre versions from several phagemid clones retrieved from the lagoon after selection was tested in a luciferase assay and compared to wild-type Cre and K201N Cre. The results demonstrate that multiple active forms of Cre recombinase were retrieved from the lagoon, including four that exhibited a reversion of the K201N mutation back to the wild-type K residue, and two that contained an activating N201D mutation.

As an evolutionary goal, a site present in the human Rosa26 locus was chosen. The Rosa 26 locus is considered a 'genomic safe harbor' locus that does not encode a protein, and allows transgenes to be inserted non-disruptively. The Rosa 26 locus further allows ubiquitous expression of inserted transgenes. See, e.g., Seidler, B. et al. 2008. *Proc. Nat. Acad. Sci. USA* 105, 10137. A site with few deviations from the native LoxP site was chosen, especially minimizing changes to important protein-DNA contacts.

Figure 5:
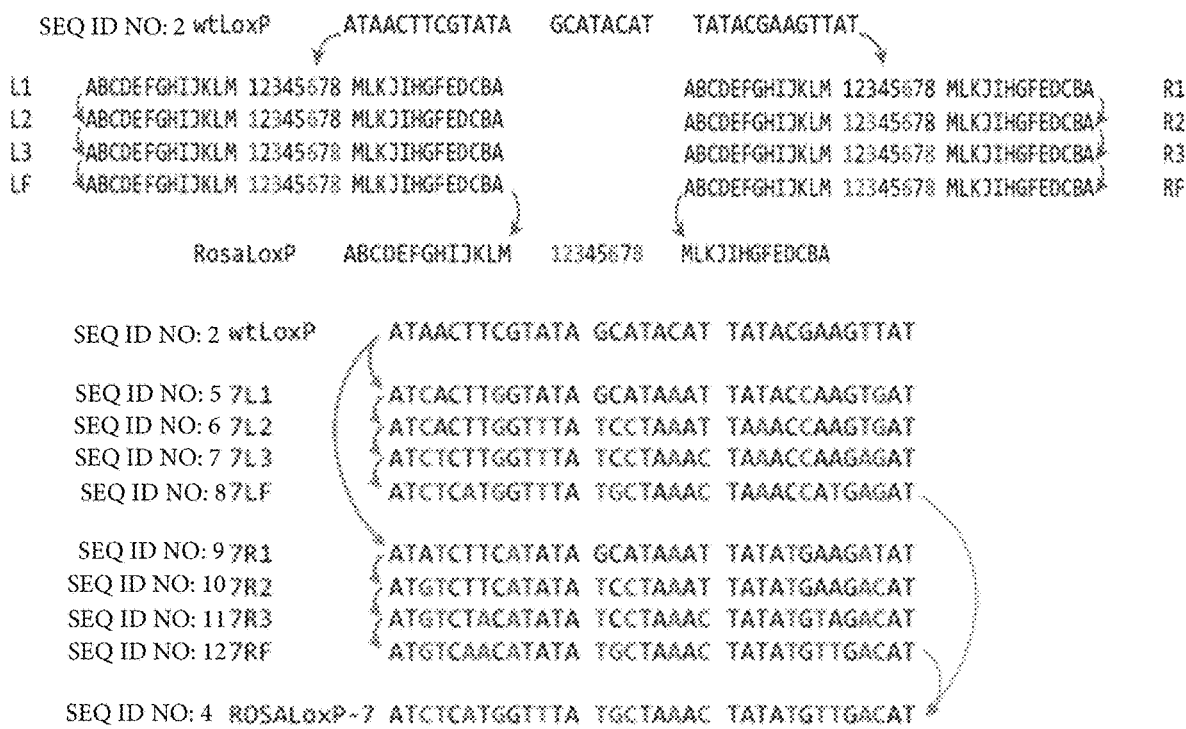
FIG. 5. Retargeting Strategy. Recombinases natively target sequences that are symmetric except for the core sequence. An illustration of the strategy for evolving Cre recombinase towards the asymmetric RosaLox site is shown. The retargeting process was split into left and right arcs, making one important DNA change at each intermediate step.

The Rosa26 locus was searched for 34-base pair sequences with the fewest changes relative to the wild-type LoxP sequence using sequencing software. For example, the RosaLoxP7 site, as disclosed in FIG. 5 has 15 mismatches compared to the wild-type LoxP site. An initial list of candidate LoxP-like sites was compiled, and from this list, sites having the fewest substitutions at positions within the LoxP site known to be most important for Cre binding (B. Thyagarajan, *Gene* 244, 47 (2000). For example, wild-type Cre has been reported to feature a relatively strict requirement that the central dinucleotide (positions 17 and 18 in the LoxP site) be TA, so LoxP-like sites without these two nucleotides in these positions were disregarded as candidates for the initial screen.

Recombinases natively target sequences that are symmetric except for the core sequence. The target sequence in the Rosa locus, termed RosaLox, was asymmetric, however. To evolve Cre towards the asymmetric RosaLox site, the retargeting evolution strategy was split into left and right arcs, and the required changes in target DNA sequence from wild-type loxP to RosaLox were introduced step by step, as outlined in FIG. 5. The left and right arcs were evolved independently. Left-arc clones were evolved on the 7L1, L2, L3, and L4 substrates, while right-arc clones were evolved on the 7R1, R2, R3, and R4 substrates. The core or spacer region was evolved in parallel in both arcs. For example, the core sequence mutations in 7L1 were mimicked in 7R1, etc. (see FIG. 5, lower panel).

Figure 6:
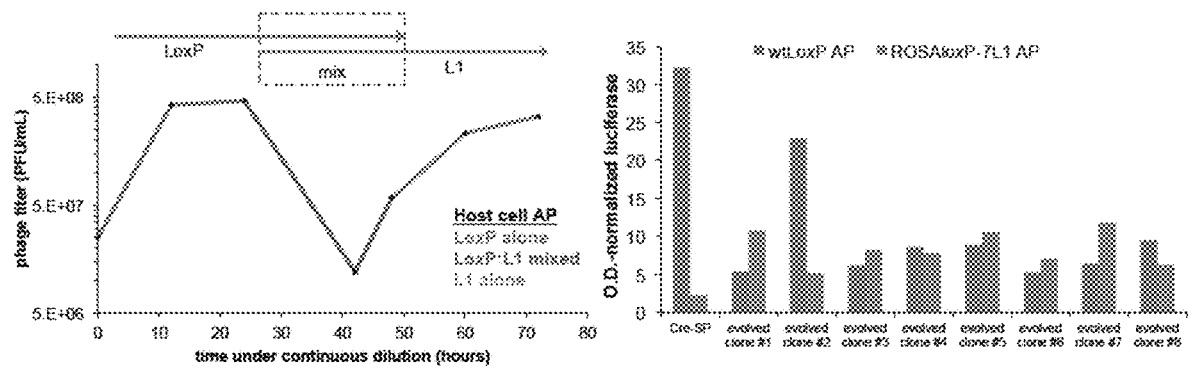
FIG. 6. Evolution of the L1 Intermediate.

FIG. 6 illustrates the evolution of recombinases recognizing the L1 intermediate target sequence. Selection was initially started with a wild-type LoxP AP, then with a mix of wild-type LoxP and L1 target sequence APs, and then exclusively with an AP comprising the L1 target sequence. Various evolved clones were identified and their recombinase activity on wild-type LoxP and on L1 target sequences was assessed and compared to wild-type Cre recombinase via a luciferase assay.

Figure 7:
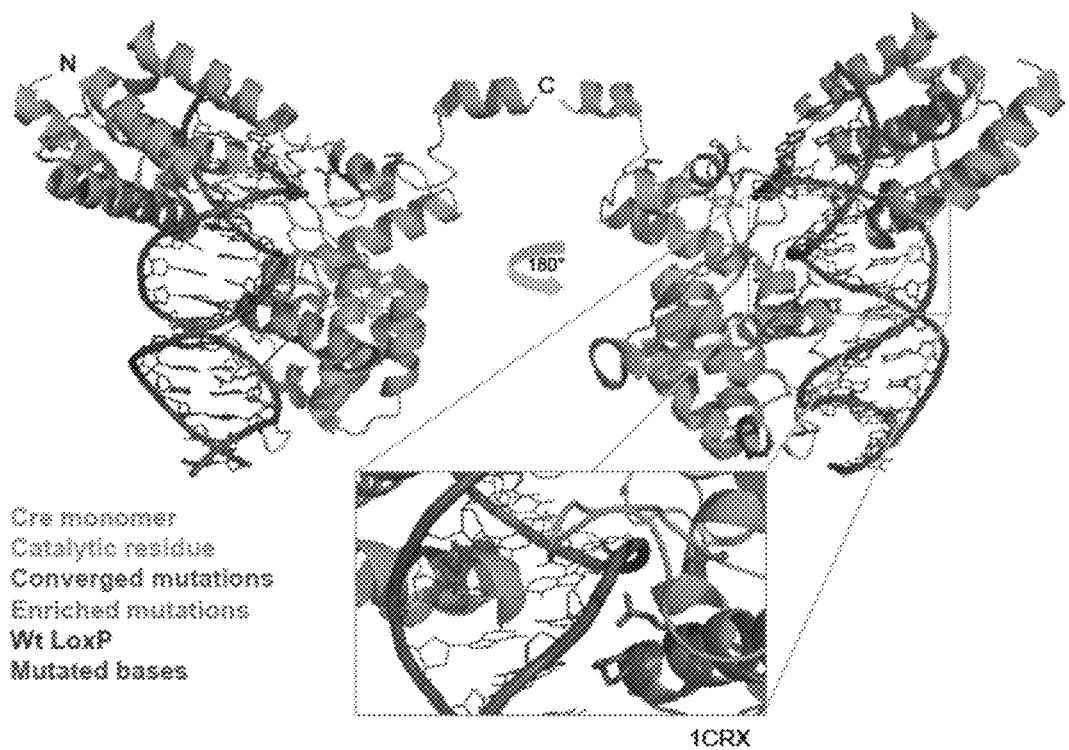
FIG. 7. Evolution of left and right arcs.

After four rounds of evolution on the left arc, thus reaching evolved clones that could recognize the LF intermediate, the mutant clones exhibited between 12-15 mutations, including 9 converged positions (shown at left in FIG. 7). The mutations were enriched at the site of protein-DNA contacts where the nucleotide had changed (see insert). Several mutations clustered around the catalytic tyrosine. Similar results were obtained from the right arc workflow after reaching the RF intermediate. However, only 3 converged mutations were required for the RF intermediate, indicating a lower barrier to recombining the RF site. It was observed that both LF- and RF-evolved clones retained significant activity on the wild type LoxP site.

Clones from the LF arc could propagate in PACE on host cells containing the RosaLox AP. Further evolved clones had several new converged mutations, as well as 3-5 commonly mutated positions.

Figure 8:
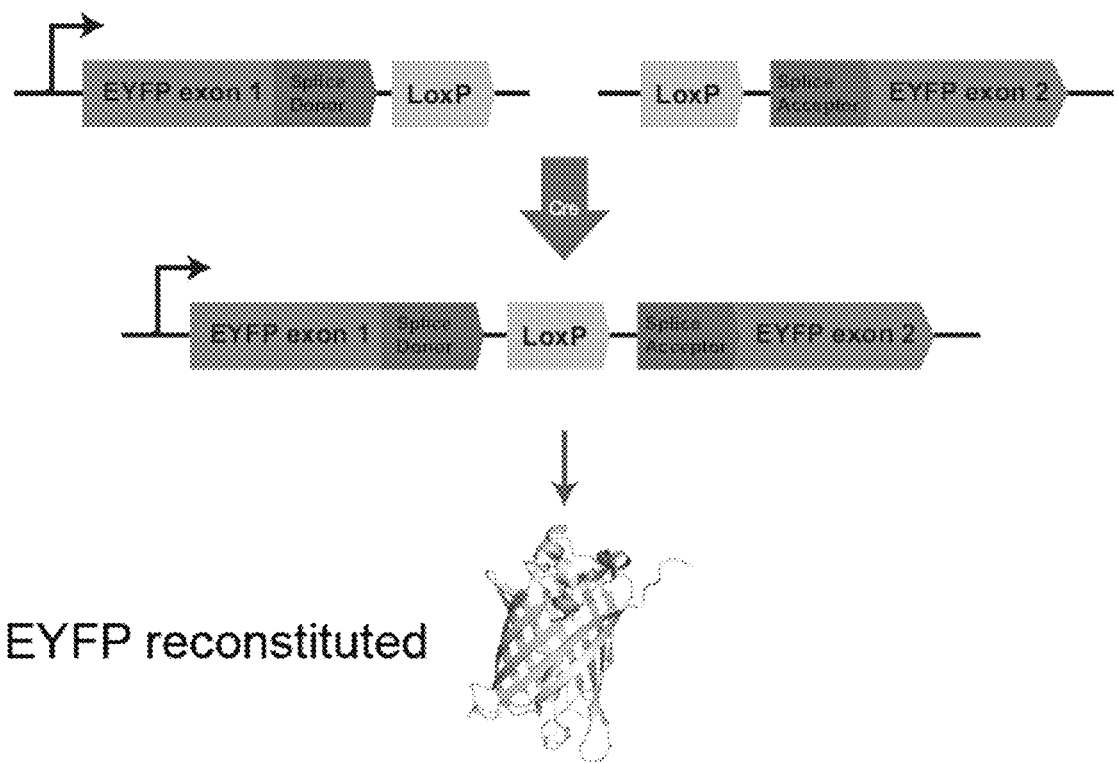
FIG. 8. Schematic illustration of a plasmid-based reporter for assessing the activity of Cre recombinases.
Figure 9:
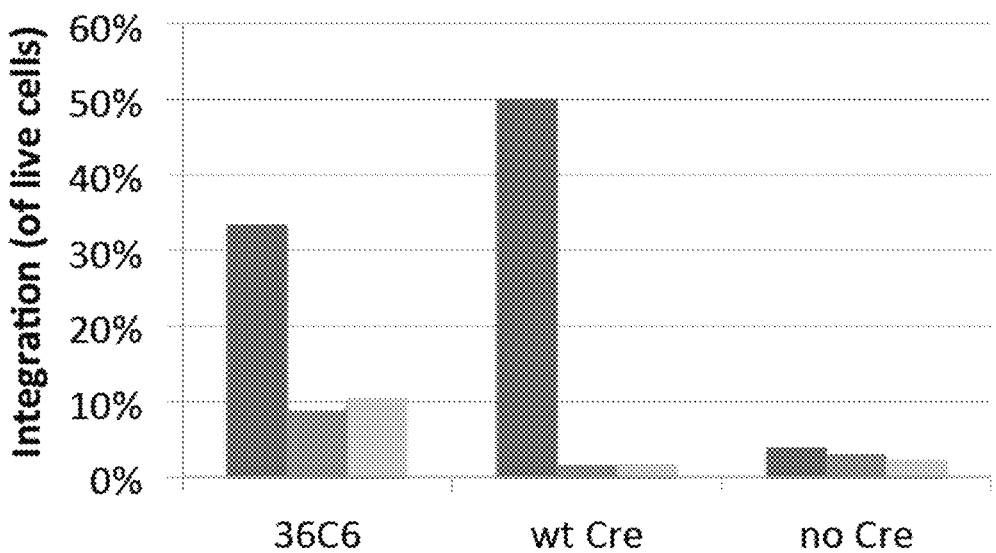
FIG. 9. Measurements of integration activity on the RosaLox site in transiently transfected HEK293 cells.

Using a newly developed mammalian plasmid-based reporter system, it was possible to measure activity on the RosaLox site in transiently transfected HEK293 cells. Recombinase activity results in integration of both constructs to form a functional expression construct encoding YFP (FIG. 8). The bar graph in FIG. 9 shows data from the YFP integration reporter. Improved integration efficiency was observed with altered recombinase target sites, including the invRosa site, which comprises an inverted core.

A plasmid encoding RosaCre clone (36C6) was co-transfected with a plasmid carrying a RosaLox site and a neomycin resistance cassette. After two weeks of neomycin (G418) selection, only HEK293 cells that had been transfected with both plasmids survived.

Figure 10:
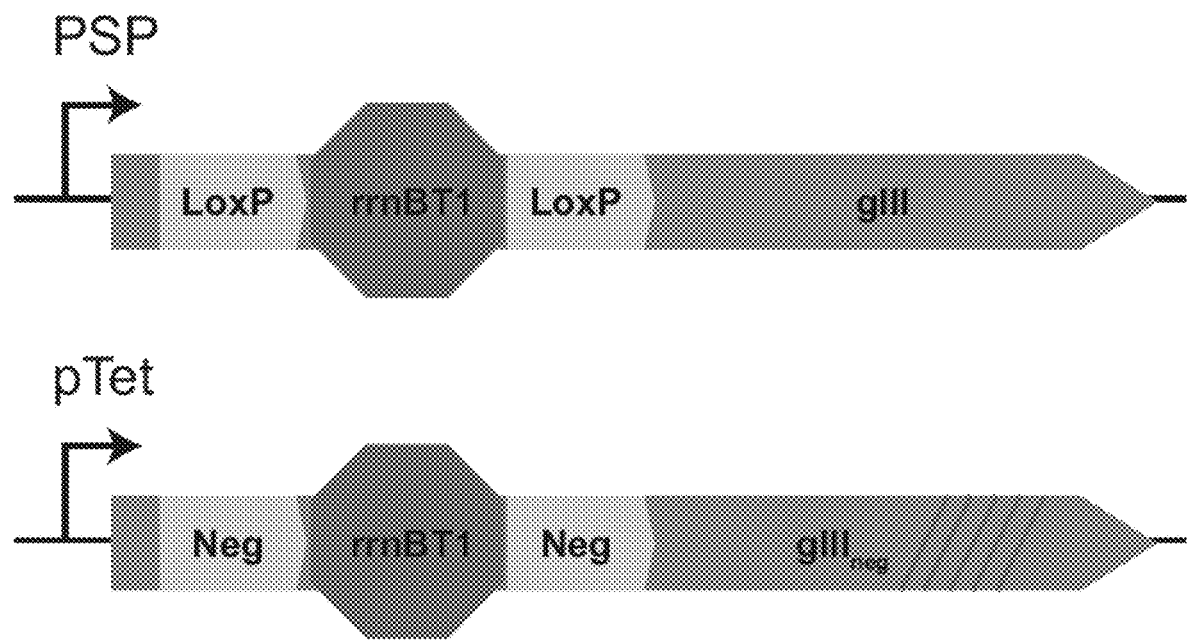
FIG. 10. Schematic illustration of an exemplary embodiment of a negative selection strategy linking unwanted recombinase activity to the production of the dominant negative pIIIneg.
Figure 11:
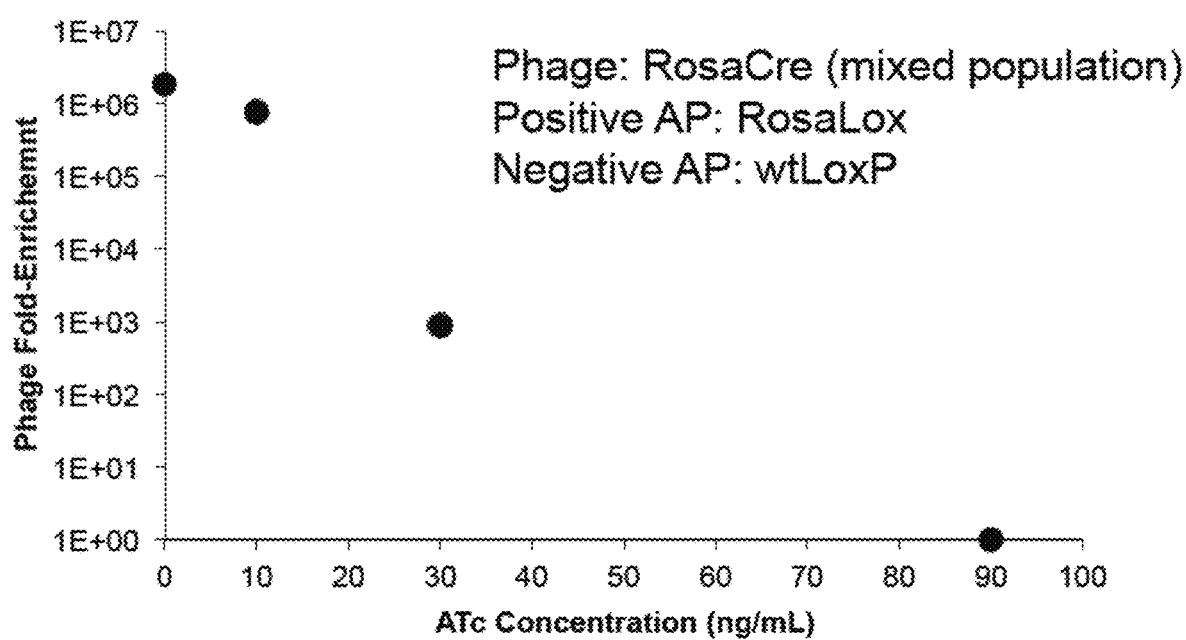
FIG. 11. Results from of an exemplary negative selection experiment.

In order to improve the specificity of the evolved recombinase clones, a negative PACE selection strategy was designed, linking unwanted recombinase activity (e.g., recognition of wild-type LoxP target sequences, to the production of the dominant negative pIIIneg (FIG. 10). The selection stringency can be adjusted by using different promoters, or by using an inducible promoter, such as the Tet-inducible promoter, and varying the dose of the inducer (e.g., anhydrotetracycline (ATc), tetracycline (Tc), or doxycycline (dox)). Results of an exemplary negative selection are illustrated in FIG. 11.

This negative selection system is useful to select against off-target activity and thus create more specific evolved Cre recombinases. In addition, such negative selection strategies can also be used to select against undesirable recombinase activity, e.g., against activity favoring the deletion of integrated genetic material. For example, recombination between the Rosa-Lox site and the invRosa site (having identical left and right half-sites as the Rosa-Lox site, but with an inverted core sequence) results in two non-identical sites, one of which is 7LF and one is 7RF. It is therefore possible, for example, to employ the selection strategies described herein to positively select for recombination between a Rosa-Lox and an invRosa-Lox site (simulating integration of a donor cassette into genomic DNA) and negatively select against recombining the RF and LF sites, simulating the possible reverse reaction (and thus deletion of inserted genomic material). The system could also be used to select for the opposite attributes (e.g., negative selection against integration and positive selection for deletion activity). The flexibility of the negative selection allows for screening out recombinase clones with unwanted activity on virtually any DNA substrate.

Figure 12:
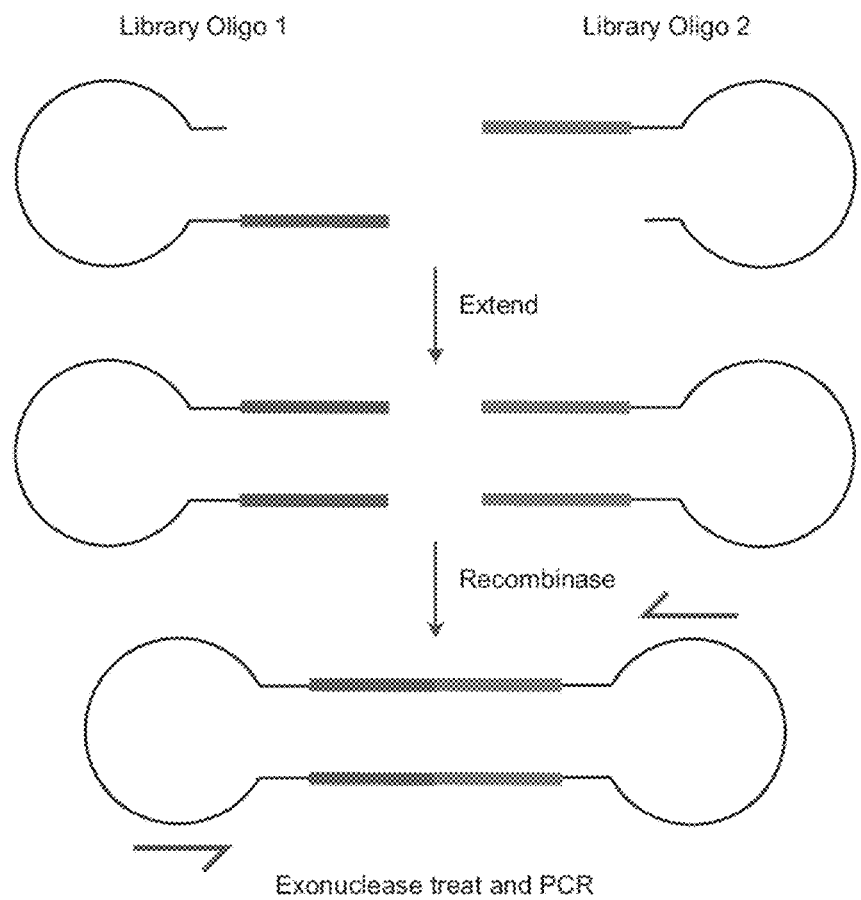
FIG. 12. Schematic illustration of an exemplary embodiment for high-throughput specificity profiling for recombinases.
Figure 13:
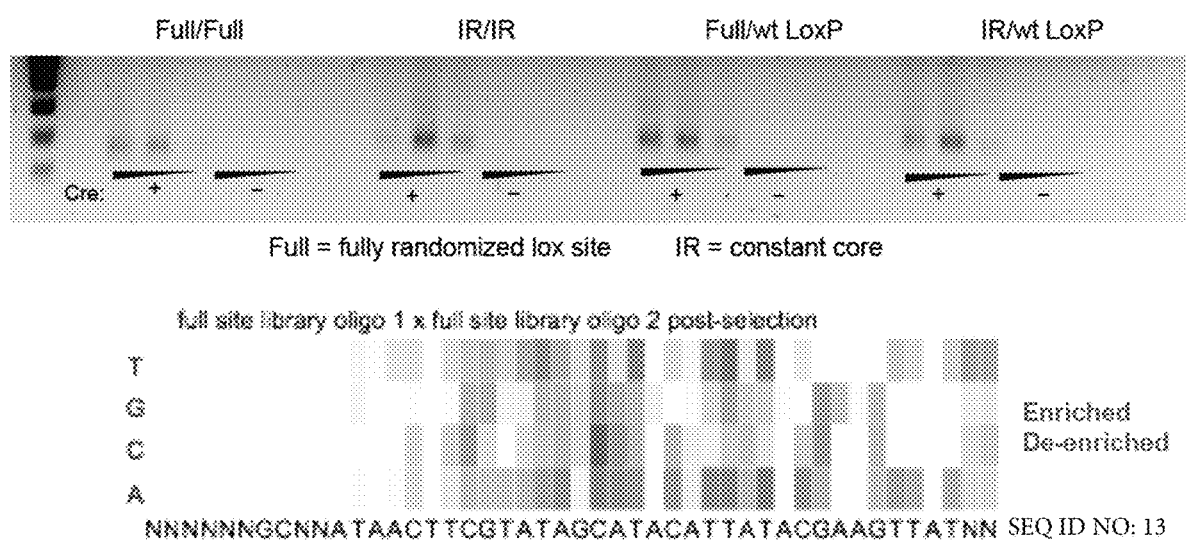
FIG. 13. Results from high-throughput sequencing of enriched PCR products were used to generate a specificity profile.

In order to assess the specificity of a recombinase, an in vitro method to measure the specificity of recombinases on randomized substrates in a library screening format was developed (FIG. 12). The PCR products resulting from recombined library members can be sequenced using high-throughput methodology in order to generate a recombinase specificity profile (FIG. 13).

Described here is one embodiment of a recombinase profiling workflow. Generally, the workflow involves three main steps: extension, recombinase treatment, and exonuclease treatment. The library oligos come in "left" and "right" versions (FIG. 12), and include a partially randomized (79% identity, 7% all other bases) recombinase target, as well as a 3' hairpin structure. For the extension step, the left and right oligos are separately extended from the hairpin across the randomized portion using Klenow exo(−) DNA polymerase. This unique step allows replication of the randomized portion as a double-stranded oligo, with a hairpin on the left or right side.

Figure 14:
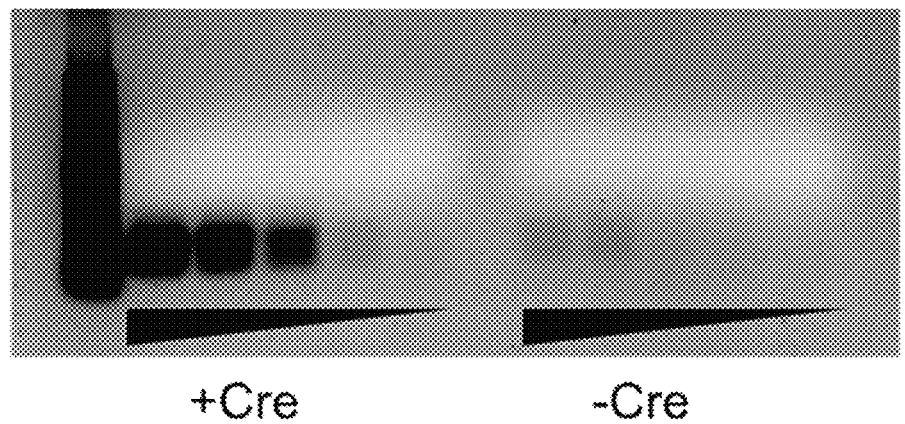
FIG. 14. Results from high-throughput sequencing of enriched PCR products used to generate a specificity profile for Cre recombinase.
Figure 15:
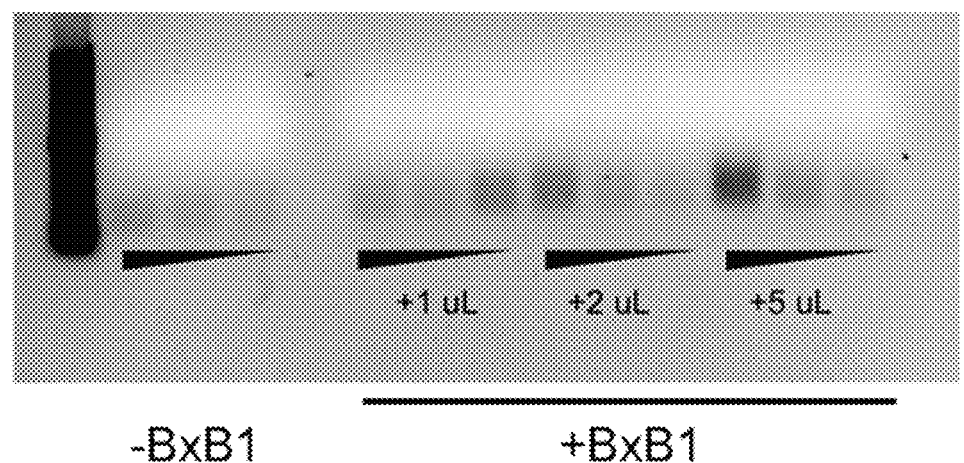
FIG. 15. Results from high-throughput sequencing of enriched PCR products used to generate a specificity profile for BxB1 integrase.

Once the oligos are double stranded, they are valid substrates for a DNA recombinase. The purified recombinase protein (e.g., Cre) is mixed with equal amounts of the left and right library oligos and allowed to react for a given amount of time. Reaction progress can be optimized, for example to stop the recombinase reaction once 25%, 50% or 75% of the substrate has been consumed. The extent of the reaction can be determined using quantitative PCR (qPCR), amplifying with forward and reverse primers which each bind a separate oligo, and thus should only amplify across recombined substrates. The protein source can be commercially obtained or expressed in vitro (e.g., using the NEB PurExpress kit). The mixture is subsequently treated with exonucleases (e.g., T7 exonuclease, Exo 1, Exo 5, RecBCD, RecJ, ExoVIII, Lambda exo, etc.) to remove any unreacted oligos. In this sense, profiling methods described herein, in some embodiments, function as a selection modality for valid recombinase substrates. After exonuclease treatment, the material can be PCR amplified and prepared for high throughput sequencing (HTS) using standard procedures. FIGS. 14 and 15 depict PCR amplification of oligos selected in the presence and absence of Cre and BxB1 integrase, respectively.

Figure 16A:
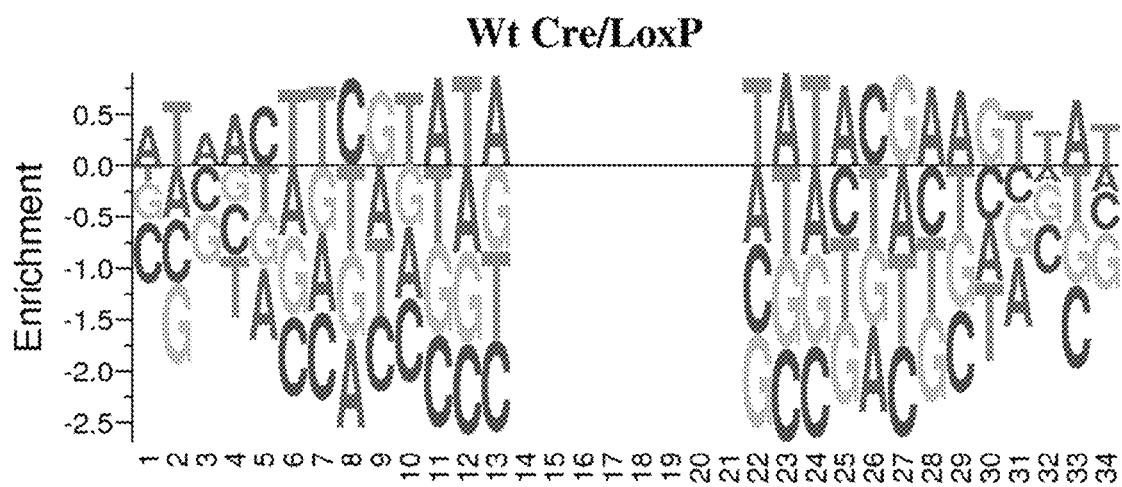
FIG. 16A. Representative data depicting sequence logos generated for LoxP site of Cre substrates. The overall specificity score is 1.38.
Figure 16B:
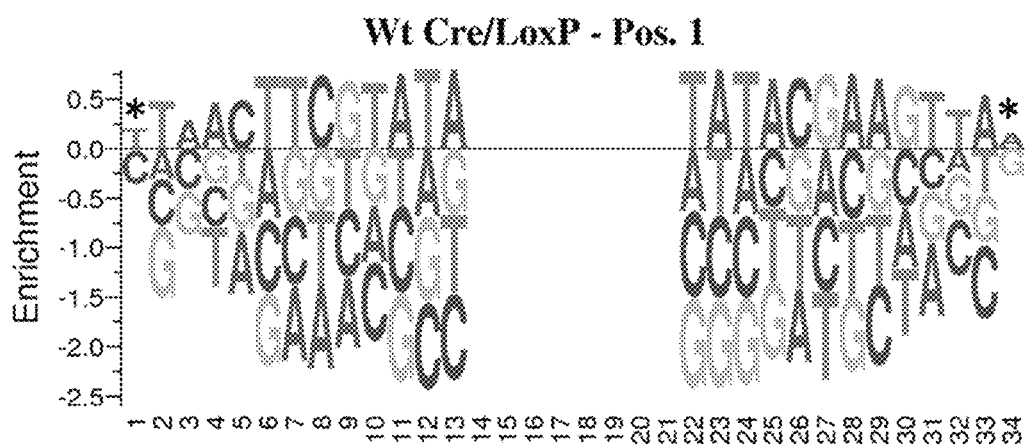
FIG. 16B. Representative data depicting sequence logos generated for LoxP site of Cre substrates at position 1.
Figure 16C:
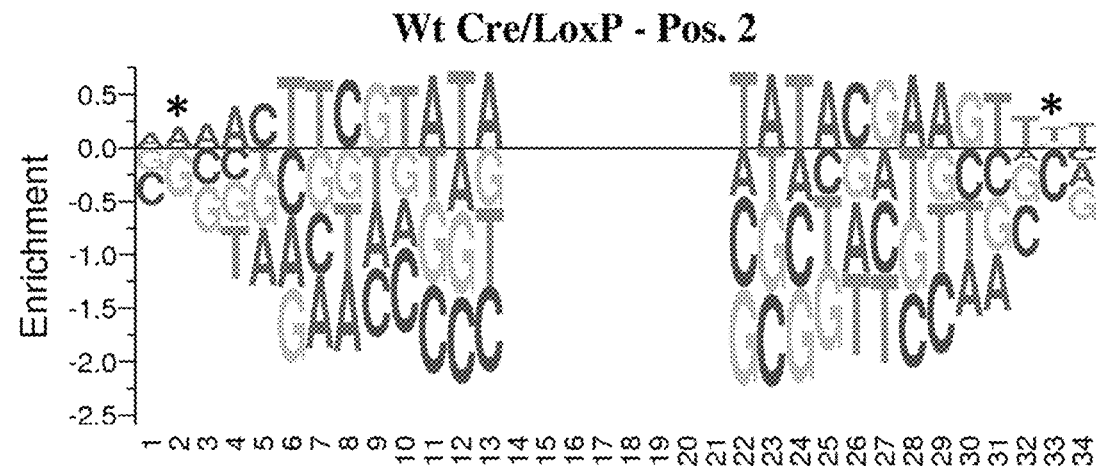
FIG. 16C. Representative data depicting sequence logos generated for LoxP site of Cre substrates at position 2.
Figure 16D:
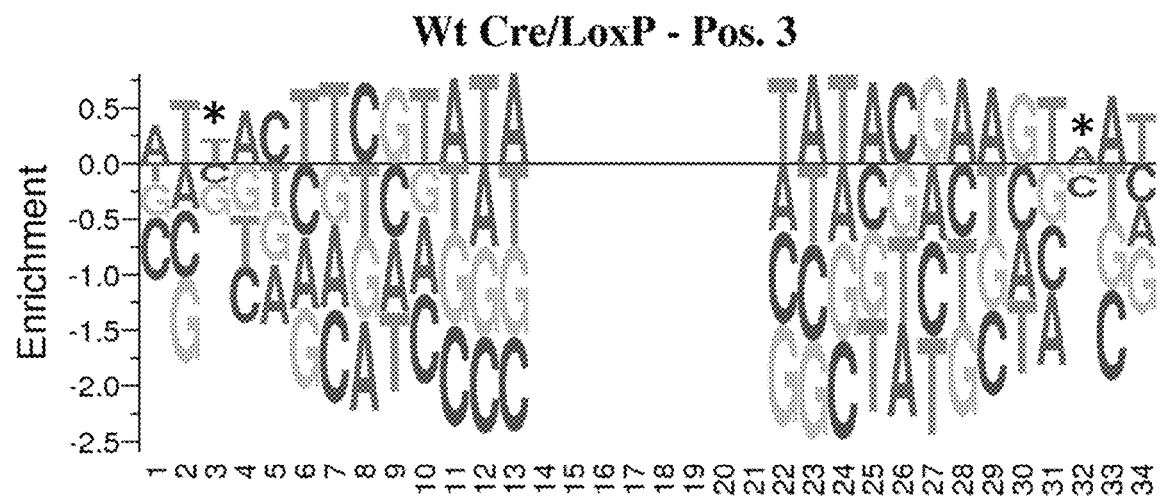
FIG. 16D. Representative data depicting sequence logos generated for LoxP site of Cre substrates at position 3.
Figure 16E:
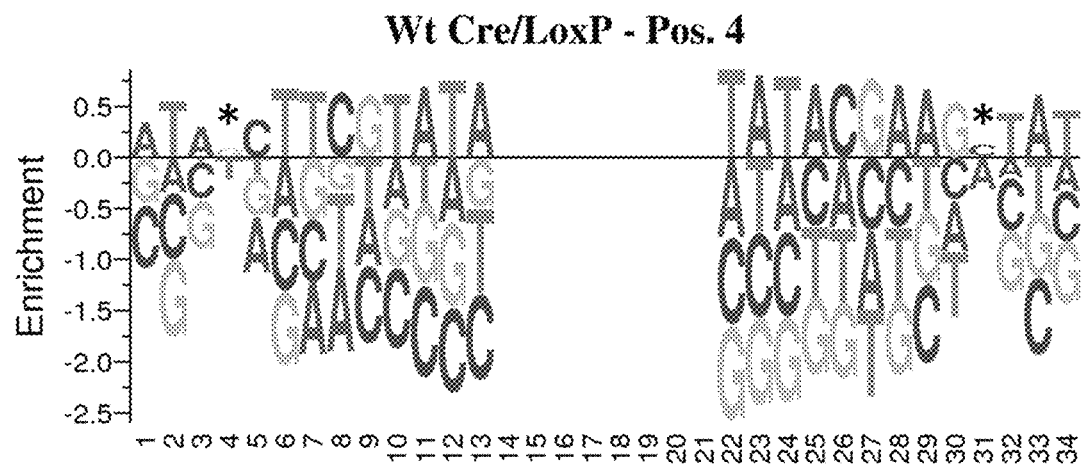
FIG. 16E. Representative data depicting sequence logos generated for LoxP site of Cre substrates at position 4.
Figure 16F:
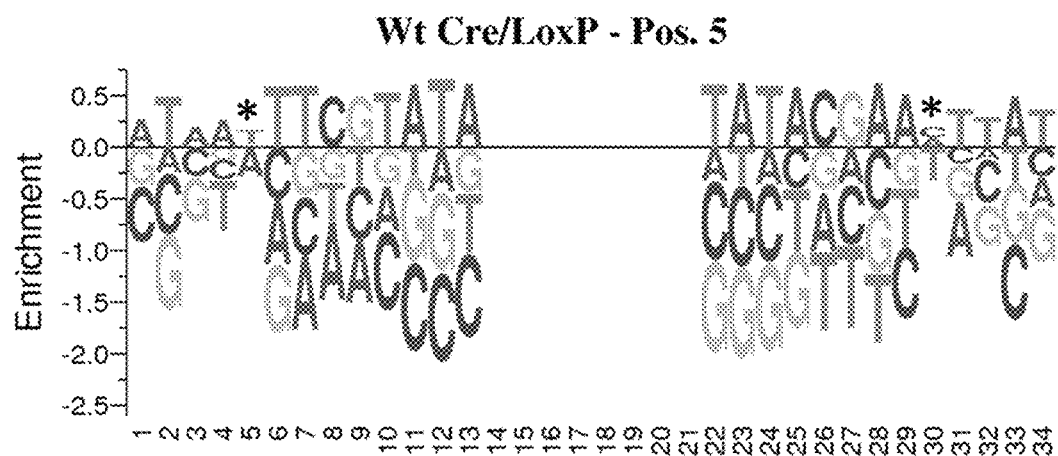
FIG. 16F. Representative data depicting sequence logos generated for LoxP site of Cre substrates at position 5.
Figure 16G:
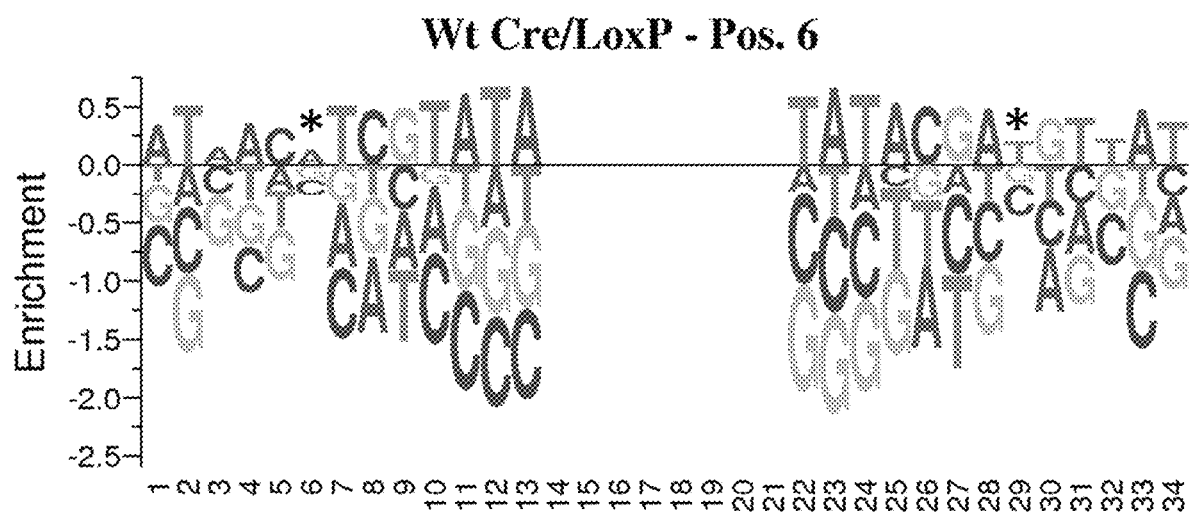
FIG. 16G. Representative data depicting sequence logos generated for LoxP site of Cre substrates at position 6.
Figure 16H:
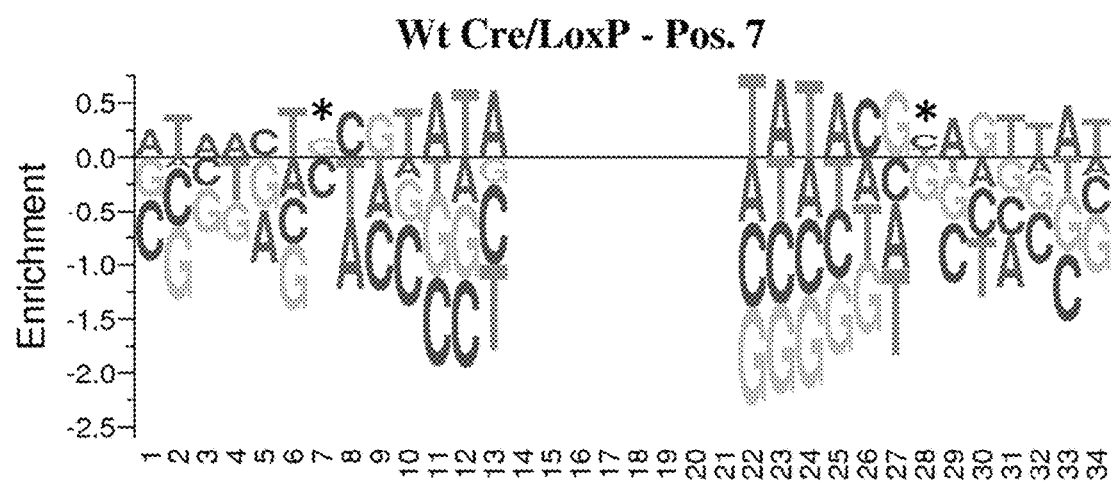
FIG. 16H. Representative data depicting sequence logos generated for LoxP site of Cre substrates at position 7.
Figure 16I:
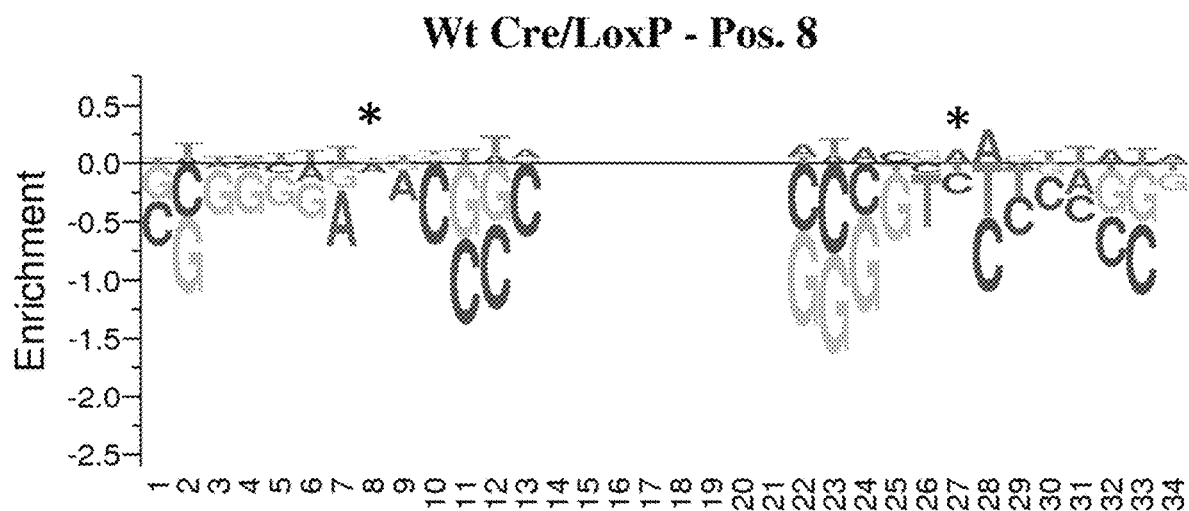
FIG. 16I. Representative data depicting sequence logos generated for LoxP site of Cre substrates at position 8.
Figure 16J:
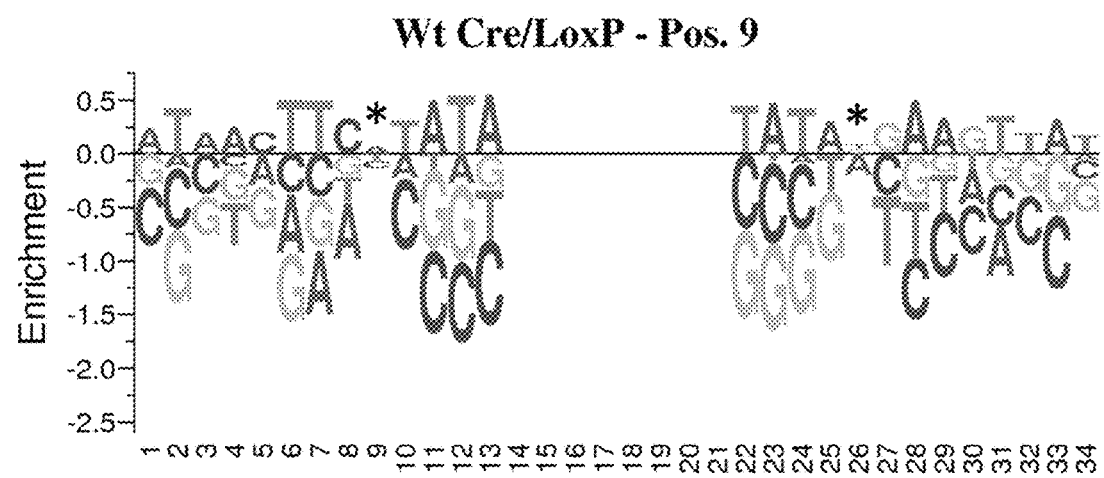
FIG. 16J. Representative data depicting sequence logos generated for LoxP site of Cre substrates at position 9.
Figure 23:
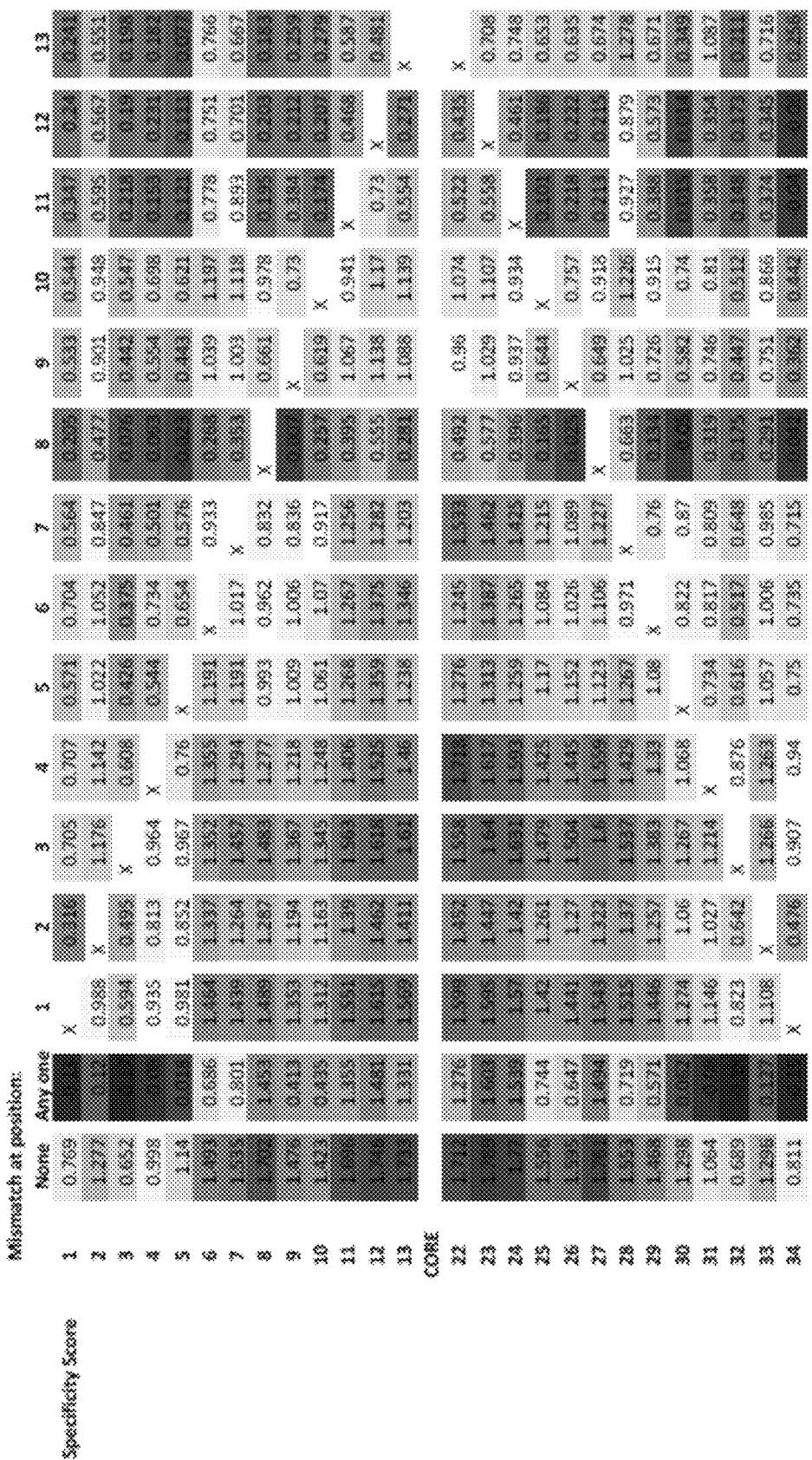
FIG. 23. Representative data depicting an alternative modality of illustrating sequence logos. The data corresponds to the sequence logos depicted in FIGS. 16A-16J.

This example describes 4 HTS experiments using Miseq v2 300 kits. Sequence logos were generated by comparing the post-selection abundance of DNA bases at each position in the lox site with the pre-selection (i.e., unreacted) abundance for each position. For example, in FIG. 16A, the canonical base at positions closest to the core are more enriched than the most distal 5 bases. This indicates that changes to the most distal bases are relatively unimportant when determining if a substrate is competent for recombination. Note the core sequence of LoxP site was held constant for these experiments, so no data is shown for the middle 8 bases. The overall specificity score is calculated by subtracting, from the enrichment factor of the correct base, the average of the enrichment of the three incorrect bases. The sequence logo depicted in FIG. 16A has an overall specificity score of 1.38. An alternative modality of presenting sequence logo data is provided in FIG. 23.

Figure 17:
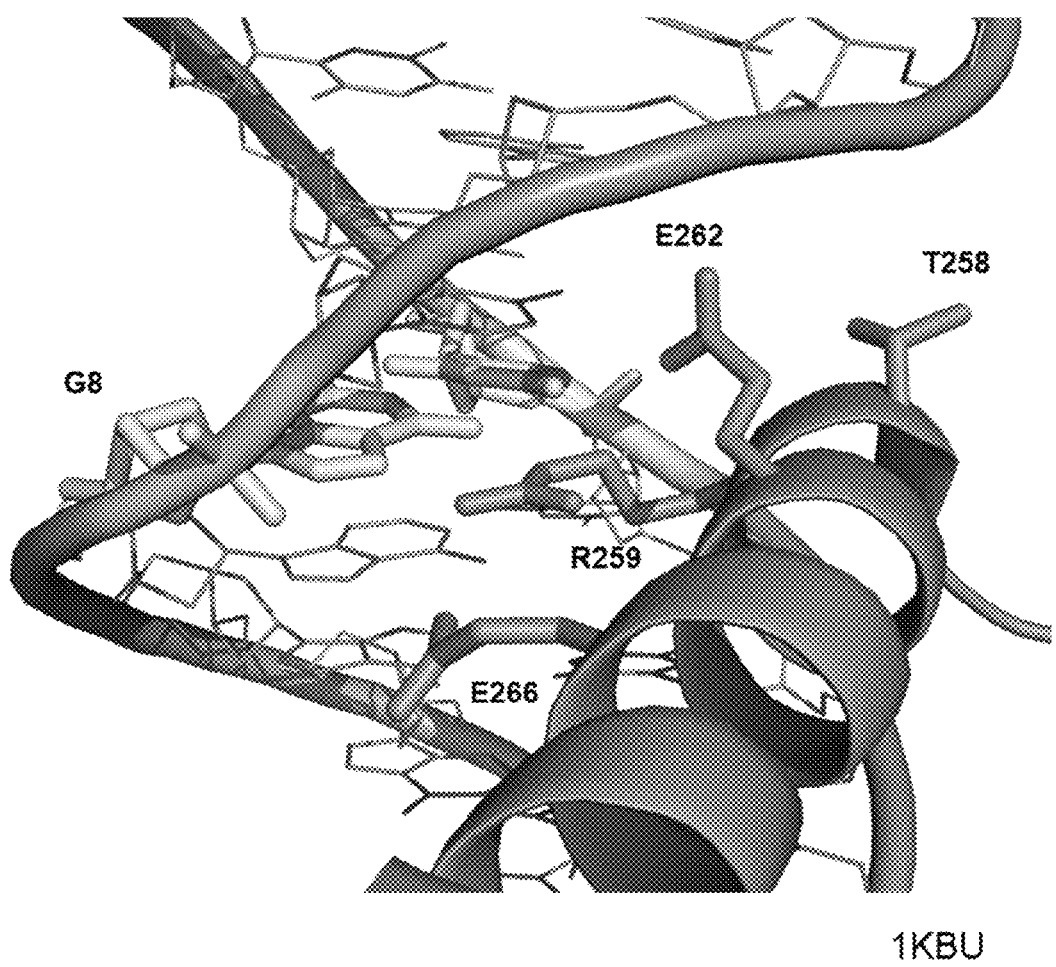
FIG. 17. Schematic illustration of crystallographic data showing several recombinase residues make specific contacts at position 8 of LoxP site.

Collecting millions of sequencing reads allows the data to be searched for hidden trends. For example, FIGS. 16B-16J show sequence logos for a subset of sequences that have a mismatch at position 1 and position 34—the first position from the right side. For the first 5 positions (FIGS. 16B-16F), there appears to be very little impact on the specificity score when a mismatch is found. This suggests a similar physical binding mode for all 5 distal bases. Relaxed specificity for the 5 distal bases is taken advantage of in the LE/RE directional recombination scheme, as confirmed by this data. Mutations at positions 6,7, and 9 (FIGS. 16G, 16H, and 16J) seem to have more of an effect on the site, but mutations at position 8 (FIG. 16I) are extremely rare in valid recombinase substrates. This agrees with crystallographic evidence that several residues (FIG. 17) make specific contacts at position 8. Table 1 shows examples of evolved CRE from the literature (e.g., as disclosed in Sarkar, I., Hauber, I., Hauber, J. & Buchholz, F. 2007. *Science* 316, 1912-5; Karpinski, J. et al. 2016. *Nat. Biotechnol.*, online pre-print; and Santoro, S. W. & Schultz, P. G. 2002. *Proc. Natl. Acad. Sci. U.S.A.* 99, 4185-90). When these mutants were evolved on substrates with changes at position 8, they all mutated the residues implicated in contacting that position (e.g., position 8).

TABLE 1

|  | Pos 8 | Res 259 | Res 262 | More |
| --- | --- | --- | --- | --- |
| wt Cre | C/G | R | E |  |
| RF | C/G | R | A |  |
| LF | G/C | C | A |  |
| Rosa | G/G | C/Y/F | A | E266K |
| M7 | T/A | S | G/H | T258N/L |
| (s)Tre | C/C | Y | Q | (G263R) |
| Brec | T/C | D | R | A260V G263K |

Figure 18:
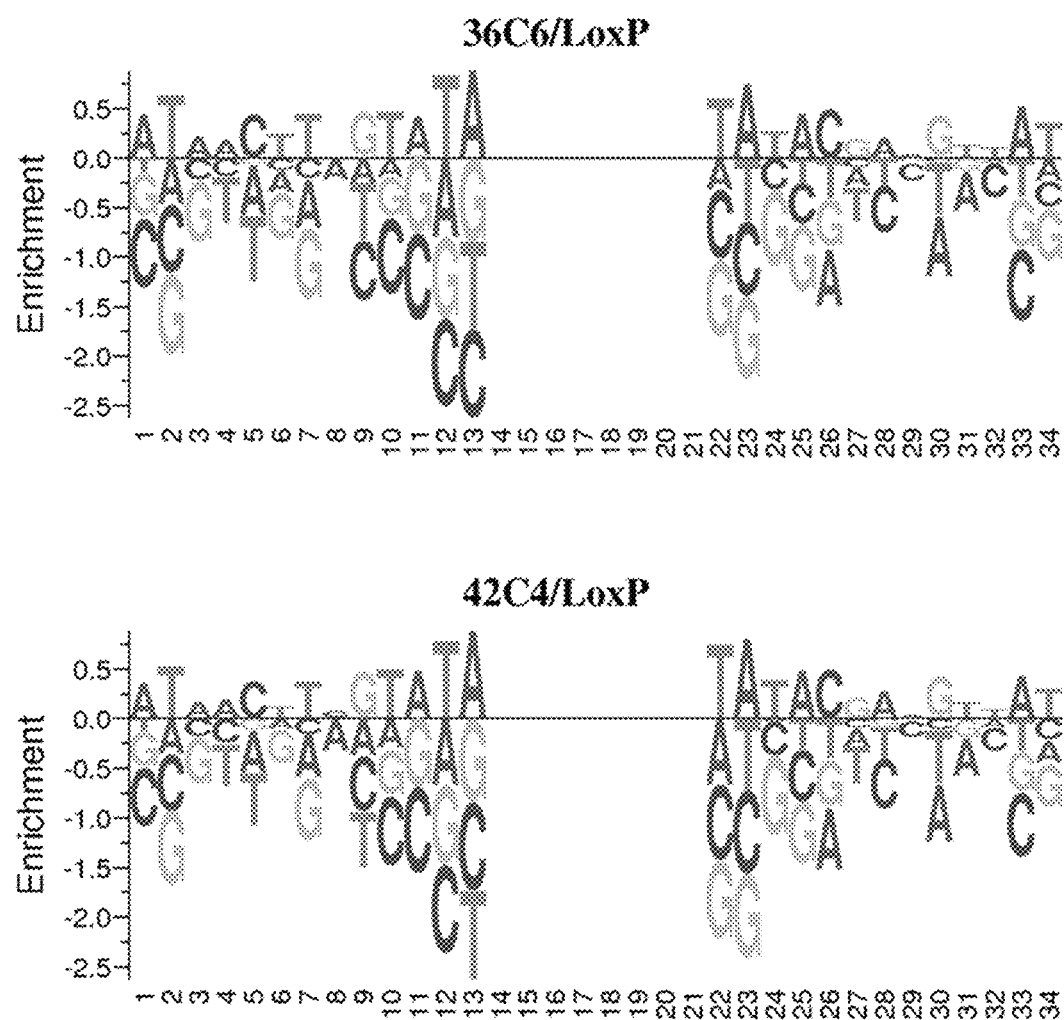
FIG. 18 Representative data depicting sequence logos of LoxP sites profiled with Cre mutants, EV36C6 and EV42C4.
Figure 19:
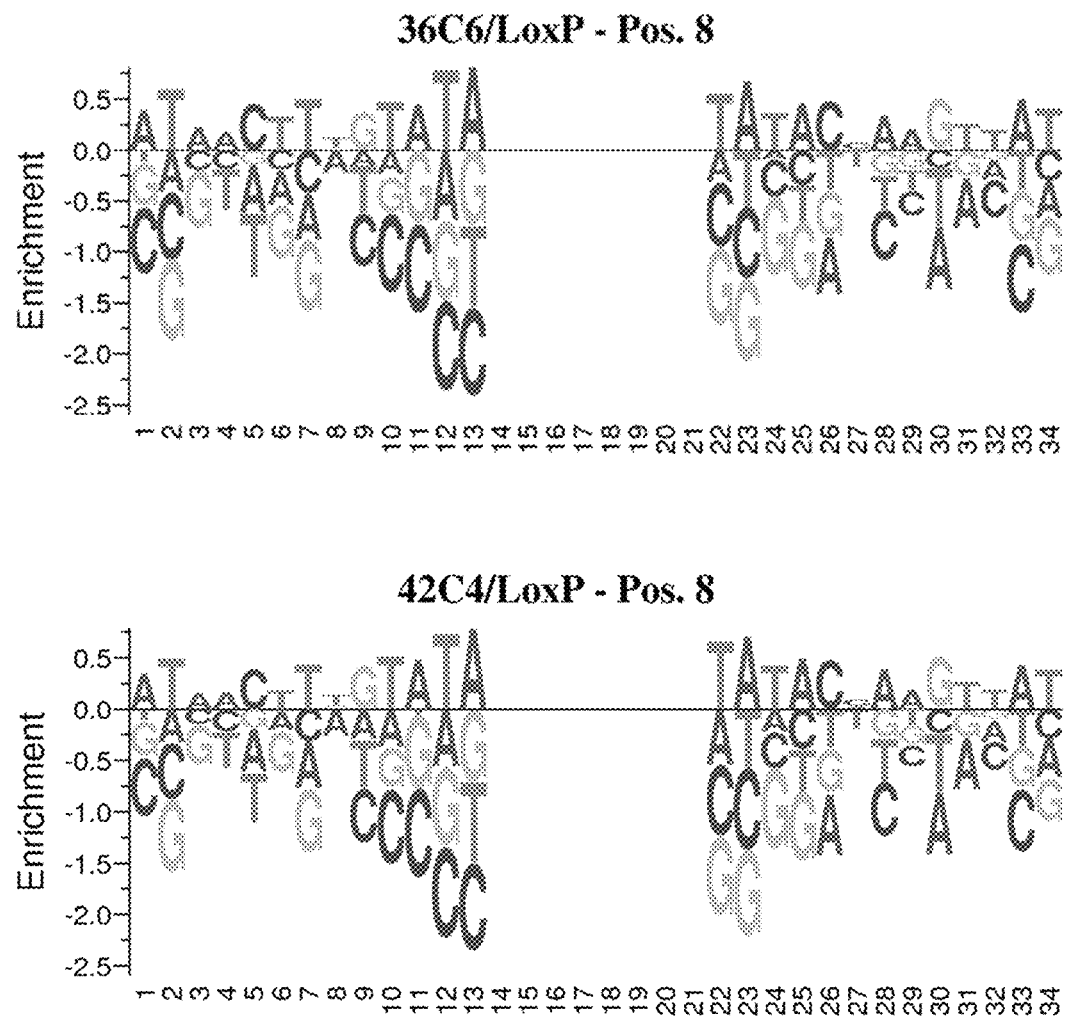
FIG. 19 Representative data depicting sequence logos of LoxP sites profiled with Cre mutants, EV36C6 and EV42C4, at position 8.
Figure 20:
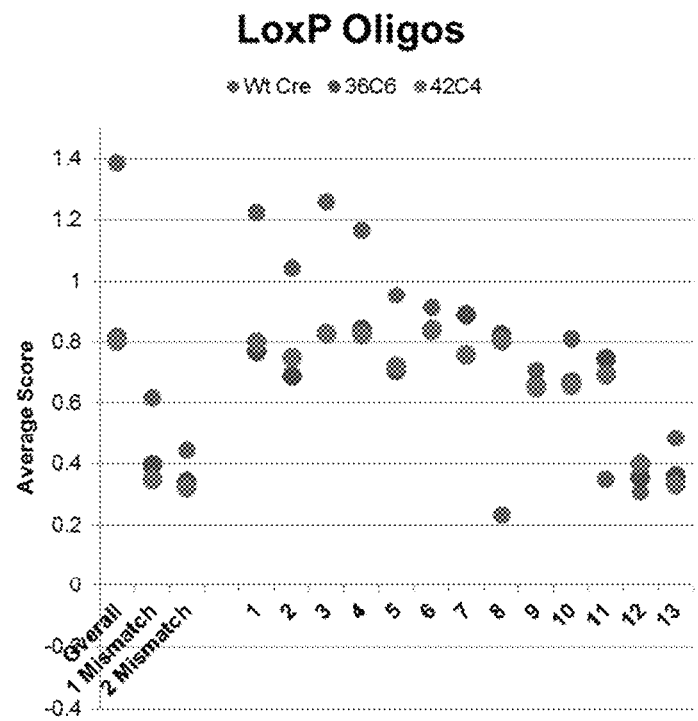
FIG. 20. Representative data depicting that Cre mutants have exaggerated reliance on binding positions 12 and 13.
Figure 20:
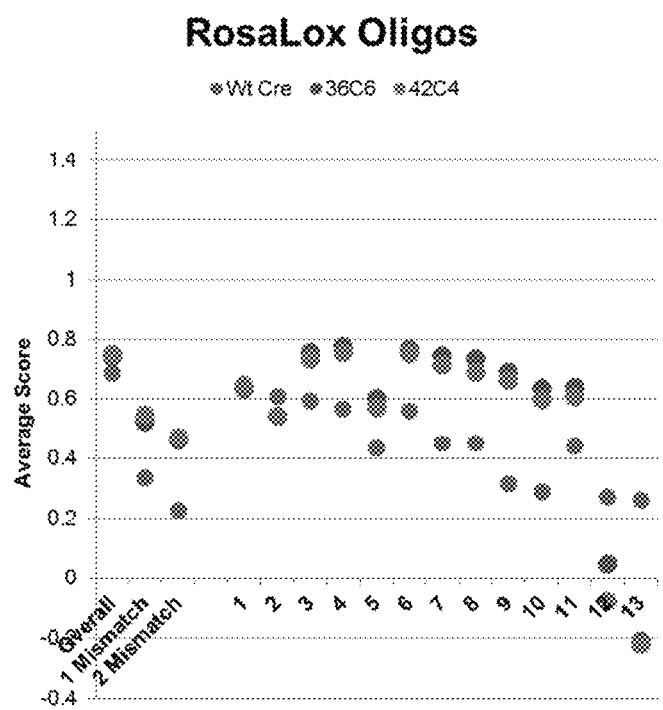
Figure 21:
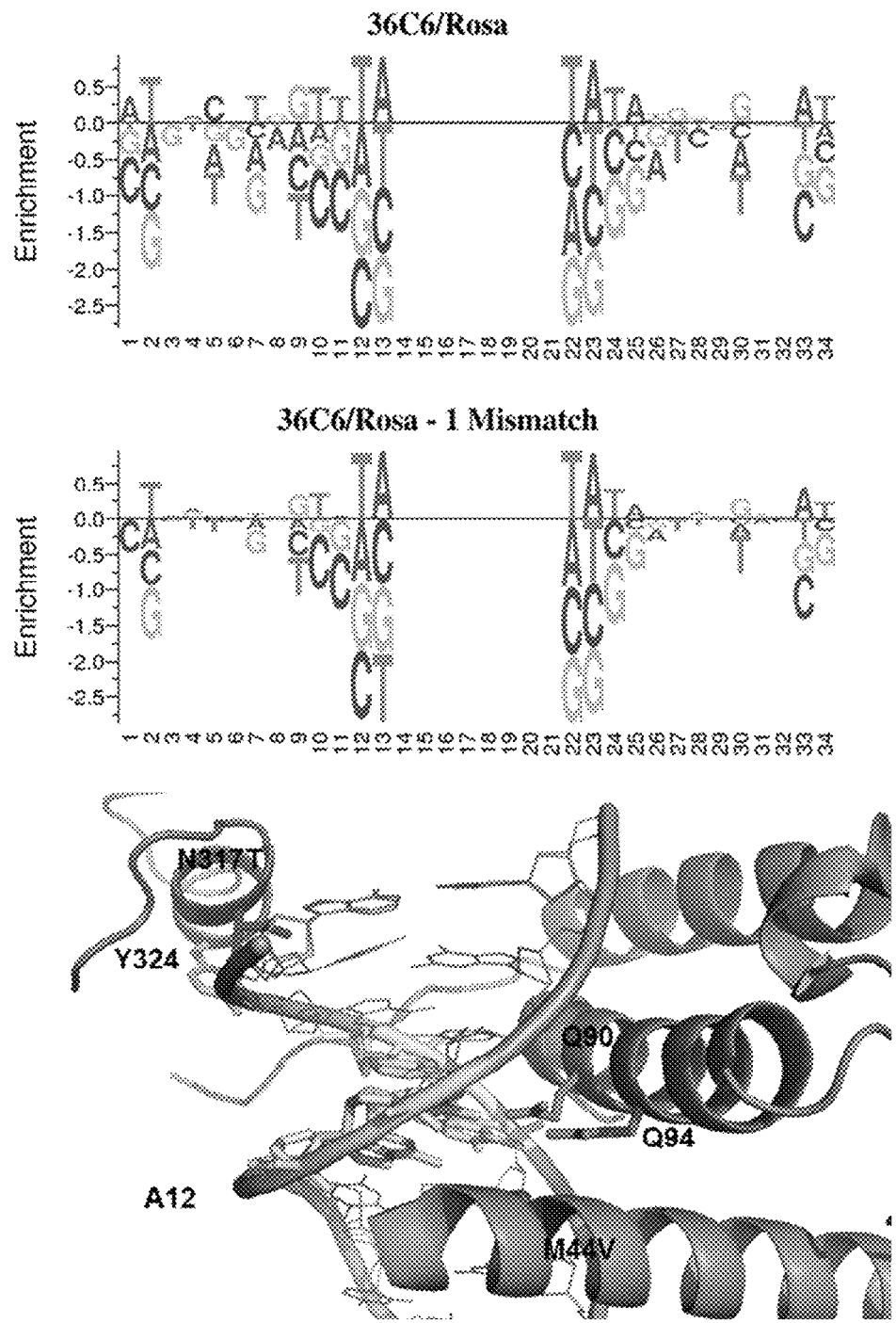
FIG. 21. Representative data depicting Cre has a higher preference for LoxP oligos and Cre mutants EV36C6 and EV42C4 have a higher preference for RosaLox oligos.

Parallel profiling experiments using two evolved Cre mutants, EV36C6 and EV42C4 were performed (FIG. 18). As shown in FIGS. 19-20, the mutants are less specific than Cre for the LoxP oligos, but more specific for the RosaLox oligos than Cre. The profiling also reveals that these two mutants have lost the strong preference at position 8 (FIG. 19), allowing them to recombine RosaLox but also making them more promiscuous. The profiling reveals that, when the substrates of the two mutant Cre's that contain 1 global mismatch are plotted, the mutant Cre's have an exaggerated reliance on binding positions 12 and 13 (FIG. 21), suggesting a unique binding mode for those two bases that has been conserved through our evolutions. Data indicates the exact residues that enforce specificity at nucleotides 12 and 13 are less clear than at position 8.

The relationship between a DNA-binding protein and its nucleic acid substrate is also investigated using specificity profiling. For example, in some embodiments, the question of how Cre binds its DNA is investigated by systematically mutating all of the residues in Cre that contact the DNA to alanines, and profiling the specificity of each single mutant. In some embodiments, the figure of reported Cre-DNA contacts from crystal structures provided by Buchholz and colleagues (Chem. Rev 2016) is used; most of the mutant residues are changed to alanines and then sequence logos are generated for each. In some embodiments, profiling methods described by the disclosure are used to determine the specificity for relatives of Cre (e.g., Flp, Dre, Tre and Brec1), which have been minimally studied. GinBeta (Barbas NAR 2010), phiC31, and BxB1 of the serine-recombinases can also be studied using profiling methods described by the disclosure.

Figure 22:
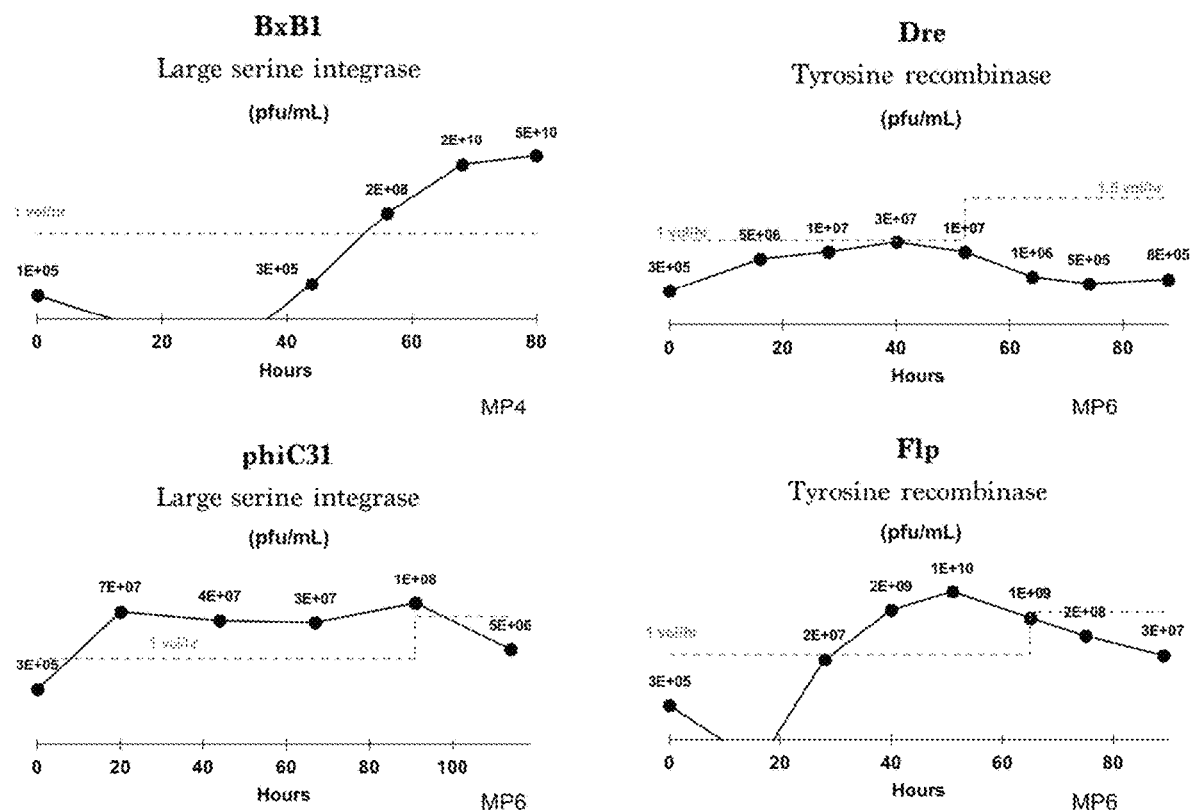
FIG. 22. Representative data depicting results of PACE experiments for the evolution of BxB1, Dre, phiC31 and Flp.

Several of the above-noted recombinases (e.g., BxB1, Dre, phiC31, Flp) have been inserted into an SP vector and have been shown to be capable of surviving in PACE (FIG. 22). The selections for each are analogous to that of Cre, with the cognate recombinase target swapped out for LoxP in the APs. The selections were carried out on the wt substrate for each recombinase. However, such recombinases could also be evolved on new substrates.

The wild-type Cre protein sequence used in the Examples section is provided below:

(SEQ ID NO: 1)
*MSNLLTVHQNLPALPVDAT*SDEVRKNLMDMFRDRQAFSEHTWKMLLSVCR

SWAAWCKLNNRKWFPAEPEDVRDYLLYLQARGLAVKTIQQHLGQLNMLHR

RSGLPRPSDSNAVSLVMRRIRKENVDAGE<u>RAKQALAFERTDFDQVRSLME</u>

<u>NSDRCQDIRNLAFLGIAYNTLLRIAEIARIRVKDISRTDGGRMLIHIGRT</u>

<u>KTLVSTAGVEKALSLGVTKLVERWISVSGVADDPNNYLFCRVRKNGVAAP</u>

<u>SATSQLSTRALEGIFEATHRLIYGAKDDSGQRYLAWSGHSARVGAARDMA</u>

<u>RAGVSIPEIMQAGGWTNVNIVMN</u>[Y]<u>IRNLDSETGAMVRLLEDGD</u>

The protein comprises an N-terminal unstructured sequence (italicized), an N-terminal domain (bold), and a C-terminal domain (underlined). The catalytic tyrosine 324 (Y324) is boxed.

Exemplary Mutations for some of the evolved Rosa Cre clones are provided below: Clone ID Mutations EV36C6 M44V, A53E, F142L, G198S, R241G, A249V, R259C, E262A, I306L, I320M EV42C4 M44V, A53E, E69A, A112V, V182I, G198S, A231T, R241Q, A249V, R259C, E262A, I306L, N317T, I320M Other mutations commonly observed amongst evolved RosaCre clones included, without limitation, Y77A, T268A, E262G, R259C/Y/F, D277N, D278N, E266K/G, S152N, R24L, V23F, A285D, D29A, E129D/G.

The Sequence of the ROSALoxP-7 site is ATCT-CATGGTTTA TGCTAAAC TATATGTTGACAT (SEQ ID NO: 4).

REFERENCES

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method for evolving a recombinase, the method comprising (a) contacting a population of host cells with a population of phage vectors comprising a gene encoding a recombinase and deficient in at least one gene for the generation of infectious phage particles, wherein (1) the host cells are amenable to transfer of the phage vector; (2) the vector allows for expression of the recombinase in a host cell, can be replicated by the host cell, and the replicated vector can transfer from host cell to host cell; (3) the host cells express a gene product encoded by the at least one gene for the generation of infectious phage particles of (a) in response to the recombination of a recombinase target sequence by the recombinase, and the level of gene product expression depends on the activity of the recombinase towards the target sequence; (b) incubating the population of host cells under conditions allowing for mutation of the gene encoding the recombinase and the transfer of the phage vectors from host cell to host cell, wherein host cells are removed from the host cell population, and the population of host cells is replenished with fresh host cells that do not harbor the phage vector; (c) isolating a replicated phage vector from the host cell population in (b), wherein the replicated vector comprises a mutated version of the gene encoding the recombinase, wherein the host cells harbor an expression construct comprising a nucleotide sequence encoding a gene product of the at least one gene for the generation of infectious phage particles of (a) under the control of a heterologous promoter and a transcriptional terminator flanked by two recombinase target sequences, wherein the recombinase target sequences are different from the target sequences recognized by the wild-type version of the recombinase, wherein recombination of the recombinase target sequences results in excision of the transcriptional terminator and expression of the at least one gene for the generation of infectious phage particles, wherein the phage vector is a filamentous phage, wherein the phage vector is an M13 phage, an fl phage, or an fd phage, wherein the at least one gene for the generation of infectious phage particles comprises a sequence encoding a pIII protein.

2. The method of claim 1, wherein the recombinase is a Cre recombinase.

3. The method of claim 1, wherein the replicated vector isolated in (c) encodes a mutated recombinase that cleaves the recombinase target sequence with higher efficiency than the version of the recombinase of (a).

4. The method of claim 1, wherein the recombinase target sequence comprises a sequence occurring in the Rosa 26 locus of the target cell.

5. The method of claim 1, wherein the recombinase target sequence comprises a sequence occurring in a genomic locus that is expressed only in cells associated with a disease or disorder.

6. The method of claim 1, wherein the host cells comprise an accessory plasmid, and together the phage vector of (a) and the accessory plasmid comprise all genes required for the generation of an infectious phage.

7. The method of claim 1, wherein the method further comprises a negative selection for undesired recombinase activity.

8. The method of claim 7, wherein the host cells comprise an expression construct encoding a dominant-negative pIII protein (pIII-neg), and wherein the expression of the pIII-neg protein depends on the undesired recombinase activity.

9. The method of claim 8, wherein expression of the pIII-neg protein is activated by recombination of undesired recombinase target sequences flanking a transcriptional terminator within the expression construct encoding the pIII-neg protein.

10. The method of claim 1, wherein the host cells further comprise a mutagenesis plasmid.

* * * * *